United States Patent [19]

Speltz et al.

[11] Patent Number: 4,623,376
[45] Date of Patent: Nov. 18, 1986

[54] HERBICIDAL PYRIDAZINES AND METHOD FOR CONTROLLING UNDESIRABLE PLANT SPECIES

[75] Inventors: Laurine M. Speltz, Princeton; Bryant L. Walworth, Pennington, both of N.J.

[73] Assignee: American Cyanamid Company, Stamford, Conn.

[21] Appl. No.: 600,228

[22] Filed: Apr. 16, 1984

[51] Int. Cl.⁴ .................... A01N 33/16; A01N 33/26; C07D 237/08; C07D 237/14
[52] U.S. Cl. ........................................ 71/92; 544/224; 544/238; 544/239; 544/240; 544/241
[58] Field of Search ............... 544/224, 238, 239, 240, 544/241; 71/92

[56] References Cited

U.S. PATENT DOCUMENTS 3,790,571 2/1974 Diskus ................................ 544/241
4,340,733 7/1982 Lam .................................... 544/224

FOREIGN PATENT DOCUMENTS 1547379 11/1968 France ................................ 544/239
59-001469 1/1984 Japan .................................. 544/239

OTHER PUBLICATIONS

Jojima, CA 70: 86465k.
Auer, CA 85: 138437j.

Primary Examiner—Sidney Marantz
Assistant Examiner—Robert Benson
Attorney, Agent, or Firm—H. G. Jackson

[57] ABSTRACT

This invention relates to a method for controlling undesirable monocotyledonous and dicotyledonous plant species by applying to the foliage thereof or to soil containing seeds or other propagating organs of said plant species, a herbicidally-effective amount of a pyridazine compound. The invention also relates to novel herbicidally-effective pyridazine compounds.

20 Claims, No Drawings

HERBICIDAL PYRIDAZINES AND METHOD FOR CONTROLLING UNDESIRABLE PLANT SPECIES

This invention relates to novel pyridazines having the structure of formula I:

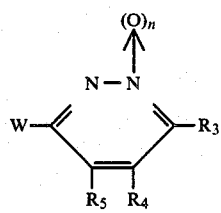

wherein $R_3$ is H, AR or $NR_1R_2$; A is S or O; R is $C_1-C_4$ alkyl or allyl; $R_1$ is $CH_3$ or $OCH_3$; $R_2$ is $CH_3$; $R_4$ is $CH_3$, $C_2H_5$ or $CH_2OCH_3$; $R_5$ is H or $CH_3$; n is 0 or 1; W is 2-thienyl, 3-thienyl, cyclohexyl or phenyl substituted with one or two substituents selected from Cl, F, $CH_3$, $OCH_3$, $CF_3$, $OCHF_2$, $OC_6H_5$ or $OCF_3$; with the proviso that n is 0 except when $R_3$ is H or $OCH_3$, then n is 0 or 1.

Preferred novel compounds of formula I are those in which $R_3$ is AR; A is O; R is $CH_3$; $R_4$ is $CH_3$; $R_5$ is H or $CH_3$; n is 0 or 1; W is

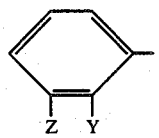

with the provisos that when Y=H, Z=Cl, F, $CH_3$, $CF_3$, $OCF_3$, $OCHF_2$ or $OCH_5$; and when Z=H, Y=Cl, F, $CH_3$; and when Y=Cl, Z=$CH_3$ or Cl.

Another preferred group of novel compounds of formula I are those in which $R_3$ is $NR_1R_2$; $R_1$ and $R_2$ are as described above; $R_4$ is $CH_3$; $R_5$ is H or $CH_3$; and W is a substituted phenyl group as described above for preferred compounds.

This invention also relates to a method for controlling undesirable monocotyledonous and dicotyledonous plant species by applying to the foliage thereof or to soil containing seeds or other propagating organs of said plant species, a herbicidally-effective amount of a compound of formula I, wherein $R_3$ is H, halogen, AR or $NR_1R_2$; A is S or O; R is $C_1-C_4$ alkyl, or allyl; $R_1$ is H, $CH_3$ or $OCH_3$; $R_2$ is H, $CH_3$, $C_2H_5$, $NH_2$ or $NHCO_2C_2H_5$; $R_4$ is H, $CH_3$, $C_2H_5$ or $CH_2OCH_3$; $R_5$ is H or $CH_3$; W is 2-thienyl, 3-thienyl, cyclohexyl, methylcyclohexyl, phenyl or phenyl substituted with one or two substituents selected from Cl, F, $CH_3$, $CF_3$, CN, $OCHF_2$, $OC_6H_5$, $OCH_3$ or $OCF_3$; with the proviso that n is 0 except when $R_3$ is H or $OCH_3$, then n is 0 or 1.

Among the most effective herbicidal agents of the present invention are the 6-phenylpyridazines depicted by formula II illustrated below:

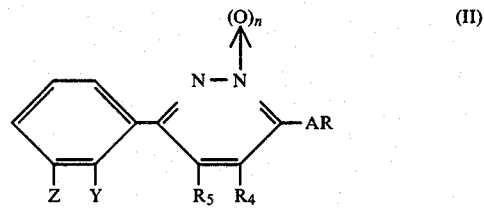

wherein A is S or O; R is $C_1-C_4$ alkyl, allyl; $R_4$ is $CH_3$, $C_2H_5$, $CH_2OCH_3$; $R_5$ is H or $CH_3$; Y and Z are each independently substituents selected from the group H, Cl, F, $CH_3$, $CF_3$, $OCH_3$, $OCHF_2$ or $OCF_3$; n=0 unless R is $CH_3$, then n=0 or 1. These formula II compounds are highly effective preemergence and postemergence herbicidal agents and are readily prepared from the corresponding 3-halo-6-phenylpyridazine. Preparation of the formula II pyridazines can generally be prepared from the 3-halo-pyridazine by displacement with an appropriate alkali metal alkoxide in a suitable solvent such as an aliphatic $C_1-C_4$ alcohol or tetrahydrofuran. The reaction mixture is usually heated to refluxing temperature under a blanket of inert gas such as nitrogen until the reaction is essentially complete, and the product is then recovered from the reaction mixture as a precipitated solid or oily residue.

Among the alkali metal alkoxides which are useful in the above procedures are sodium methoxide, potassium methoxide, sodium ethoxide, sodium isopropoxide, potassium butoxide, potassium propoxide, and the like.

Preparation of the 3-thio and 3-alkylthio-6-phenylpyridazines is accomplished in essentially the same manner as described above for the 3-alkoxy-6-phenylpyridazines, excepting that displacement from the 3-chloro-6-phenylpyridazine precursor is achieved using the appropriate mercaptide salt.

The above reactions may be graphically illustrated as follows:

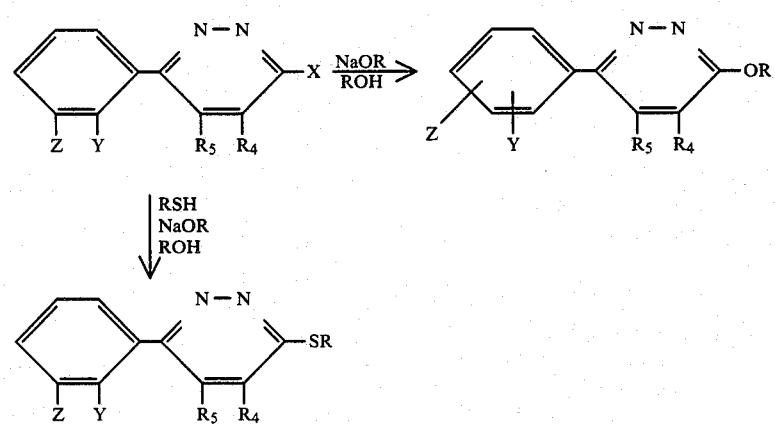

wherein X is halogen, preferably, chlorine; and $R_4$, $R_5$, Y, and Z are as described above.

Advantageously, it has been found that the 3-alkylthiopyridazine will undergo a Raney nickel reduction to provide the corresponding 3-unsubstituted pyridazine of formula III. The reaction is generally carried out in the presence of a solvent such as a $C_1-C_4$ aliphatic alcohol.

The reaction may be illustrated as follows:

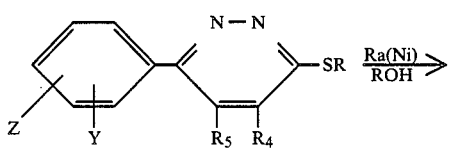

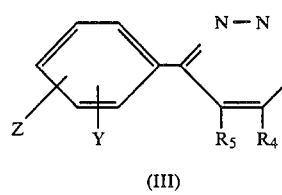

(III)

wherein R, $R_4$, $R_5$, Y, and Z are as described above in reference to formula II compounds.

The formula III 3-unsubstituted pyridazines of this invention can also be prepared from the 3-halopyridazine by hydrogenolysis thereof using a palladium on carbon catalyst. Generally the 3-halo compound is dissolved in acetic acid containing the catalyst. The mixture is then placed in a Parr hydrogenator, and the mixture is shaken until the theoretical amount of hydrogen is consumed.

This reaction may be illustrated as follows:

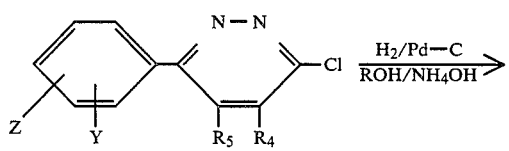

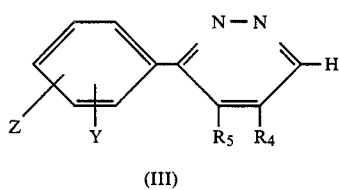

(III)

wherein $R_4$, $R_5$, Y, and Z are as defined with regard to formula II compounds.

Also in accordance with the present invention, we have found that the 3-alkoxy-6-phenylpyridazines and 3-aryloxy-6-phenylpyridazines of formula II above, and the 3-unsubstituted pyridines of formula III can be converted to their corresponding N-oxides by reaction of said compounds with m-chloroperbenzoic acid preferably in the presence of a chlorinated hydrocarbon solvent such as chloroform.

Preparation of the aminopyridazines of formula IV can be achieved by reacting the appropriately substituted 3-halo-6-phenylpyridazine with an appropriate amine in the presence of hydriodic acid at an elevated temperature generally between about 75° C. to 150° C. and at a superatmospheric pressure usually between about 75 and 125 psig. The reaction may be graphically illustrated as follows:

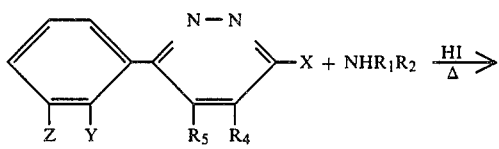

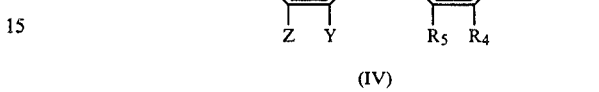

(IV)

wherein X is halogen; $R_1$ is H, $CH_3$ or $OCH_3$; $R_2$ is H, $CH_3$, $C_2H_5$ or $NHCO_2C_2H_5$; and $R_4$, $R_5$, Y, and Z are as described above in reference to formula II compounds.

The formula I compounds of this invention, which include all of the compounds of formulae II, III, and IV, are exceedingly effective preemergence and postemergence herbicidal agents useful for the control of an exceptionally wide variety of annual and perennial monocotyledonous and dicotyledonous plants. Moreover, these compounds are herbicidally effective for controlling weeds indigenous to both dry land and wet land areas. They are also useful as aquatic herbicides and are unique in their effectiveness in controlling the above-said plants when applied to the foliage thereof or to soil or water containing seeds or other propagating organs of said plants, such as tubers, rhizomes or stolons, at rates of from about 0.25 to 10.0 kg/ha, and preferably at rates from about 0.50 to 4.0 kg/ha.

It is, of course, obvious that rates of application above the 10.0 kg/ha level can also be used to effectively kill undesirable plant species; however, rates of application of toxicant above the level necessary to kill the undesirable plants should be avoided since application of excessive amounts of toxicant is costly and serves no useful function in the environment.

Effective application of the formula I pyridazines of the present invention can be achieved by applying the active ingredient to the soil or to the foliage of undesirable plants in the form of a dilute liquid spray, a dust or dust concentrate, or as a granular product.

Wettable powders, flowable liquids, and emulsifiable concentrates all lend themselves to liquid spray application. In practice, they are generally dispersed in water or other inexpensive liquid diluent and applied as a liquid spray to the locus where undesirable plants are to be controlled.

Wettable powders can be prepared by grinding together about 20% to 45% by weight of a finely-divided carrier such as kaolin, bentonite, diatomaceous earth, attapulgite or the like, 45% to 80% by weight of the active compound, 2% to 5% by weight of a dispersing agent such as sodium lignosulfonate, and 2% to 5% by weight of a nonionic surfactant such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the compounds of the invention are to be used as herbicidal agents for soil treatments, the compounds may be prepared and applied as granular products. Preparation of the granular product can be achieved by dissolving the active compound in a solvent such as methylene chloride, N-methylpyrrolidone or the like and spraying the thus-prepared solution on a granular carrier such as corncob grits, sand, attapulgite, kaolin, or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of 4-methyl-3-methoxy-6-phenylpyridazine

Sodium methoxide (243 g) is cautiously added to a solution of 3-chloro-4-methyl-6-phenylpyridazine (307 g, 1.5 mol) in 3.4 L of methanol. The mixture is heated to refluxing temperature for approximately eight hours under an atmosphere of nitrogen and then poured into water (4.5 L). The resulting precipitate is collected, washed with water, and dried to give 270 g (90%) of product with a melting point of 62°-64° C.

By a similar procedure, and using the appropriate alkali metal alkoxide and alcohol, the corresponding halopyridazines are converted to the compounds listed in Tables I and II below.

TABLE I

PREPARATION OF PYRIDAZINES HAVING THE STRUCTURE:

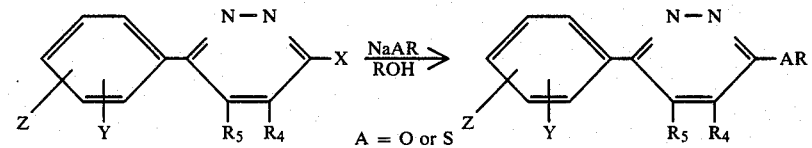

| Example | X | Y | Z | AR | $R_4$ | $R_5$ | Description | mp °C. |
|---|---|---|---|---|---|---|---|---|
| 2 | Cl | H | 3-$CF_3$ | $OCH_3$ | $CH_3$ | H | tan solid | 68–70 |
| 3 | Cl | H | 3-$CF_3$ | $OC_2H_5$ | $CH_3$ | H | yellow solid | 62–64 |
| 4 | Cl | H | 3-Cl | $OCH_3$ | $CH_3$ | H | Off-white solid | 81–82 |
| 5 | Cl | H | 3-$CH_3$ | $OCH_3$ | $CH_3$ | H | white solid | 44–46 |
| 6 | Cl | H | H | $OC_2H_5$ | $CH_3$ | H | off-white solid | 114–116 |
| 7 | Cl | H | 3-$OC_6H_5$ | $OCH_3$ | $CH_3$ | H | orange oil | — |
| 8 | Cl | H | 3-$OCH_3$ | $OCH_3$ | $CH_3$ | H | yellow oil | — |
| 9 | Cl | H | 2-Cl | $OCH_3$ | $CH_3$ | H | tan solid | 82–86 |
| 10 | Cl | 5-Cl | 3-Cl | $OCH_3$ | $CH_3$ | H | brown solid | 110–112 |
| 11 | Cl | H | 3-F | $OCH_3$ | $CH_3$ | H | yellow solid | 80–81 |
| 12 | Cl | H | 3-$CF_3$ | $OC_6H_5$ | $CH_3$ | H | tan solid | 89–93 |
| 13 | Cl | H | 4-F | $OCH_3$ | $CH_3$ | H | tan solid | 74–76 |
| 14 | Cl | H | 3-$CF_3$ | $OC_3H_7\underline{i}$ | $CH_3$ | H | yellow solid | 84–86 |
| 15 | Cl | H | H | $OCH_3$ | H | $CH_3$ | yellow oil | — |
| 16 | Cl | H | 4-Cl | $OCH_3$ | $CH_3$ | H | yellow solid | 129–130 |
| 17 | Cl | H | 3-$CF_3$ | $SC_3H_7\underline{i}$ | $CH_3$ | H | yellow solid | 123–125 |
| 18 | Cl | H | H | $SCH_3$ | $CH_3$ | H | yellow solid | 79–80 |
| 19 | Cl | H | H | $OCH_3$ | $CH_3$ | $CH_3$ | tan solid | 88–90 |
| 20 | Cl | H | H | $OC_3H_7\underline{i}$ | $CH_3$ | H | red oil | — |
| 21 | Cl | H | H | $OCH_2CH=CH_2$ | $CH_3$ | H | white solid | 60–62 |
| 22 | Cl | H | 2-$OCH_3$ | $OCH_3$ | $CH_3$ | H | beige needles | 88–90 |
| 23 | Cl | H | 2-F | $OCH_3$ | $CH_3$ | H | brown crystals | 64–66 |
| 24 | Cl | H | 2-$CH_3$ | $OCH_3$ | $CH_3$ | H | oily red solid | — |
| 24a | Cl | H | 4-$CF_3$ | $OCH_3$ | $CH_3$ | H | white solid | 110–112 |
| 24b | Cl | 2-Cl | 4-Cl | $OCH_3$ | $CH_3$ | H | white solid | 129–131 |
| 24c | Cl | H | H | $OCH_3$ | $CH_3$ | H | white solid | 49–50 |
| 24d | Cl | 3-$CH_3$ | 5-$CH_3$ | $OCH_3$ | $CH_3$ | H | rust-colored solid | 120–122 |
| 24e | Cl | H | 3-CN | $OCH_3$ | $CH_3$ | H | beige solid | 128–130 |
| 24f | Cl | H | 3-$CF_3$ | $SCH_3$ | $CH_3$ | H | white solid | 56–59 |
| 24g | Cl | H | 4-$CH_3$ | $OCH_3$ | $CH_3$ | H | yellow solid | 100–102 |
| 24h | Cl | H | 3-$CF_3$ | $OCH_3$ | $CH_3$ | H | white solid | 101–104 |
| 24i | Cl | H | 3-$CF_3$ | $OCH_3$ | $CH_3$ | $CH_3$ | yellow solid | 78–81 |
| 24j | Cl | H | 3-$OCHF_2$ | $OCH_3$ | $CH_3$ | H | yellow oil | — |

TABLE II

PREPARATION OF PYRIDAZINES HAVING THE STRUCTURE

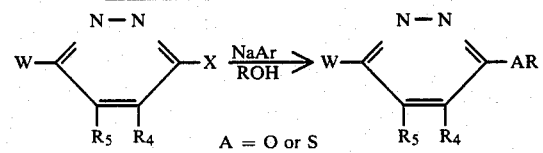

| Example | W | X | AR | $R_4$ | $R_5$ | mp °C. |
|---|---|---|---|---|---|---|
| 25 | 3-pyridyl | Cl | $OCH_3$ | $CH_3$ | H | 102–104 |
| 26 | 4-pyridyl | Cl | $OCH_3$ | $CH_3$ | H | 74–75 |
| 27 | 3-thienyl | Cl | $OCH_3$ | $CH_3$ | H | 72–74 |

TABLE II-continued
PREPARATION OF PYRIDAZINES HAVING THE STRUCTURE

W—[N=N ring]—X  $\xrightarrow{\text{NaAr} \atop \text{ROH}}$  W—[N=N ring]—AR with $R_5$, $R_4$ substituents;  A = O or S

| Example | W | X | AR | $R_4$ | $R_5$ | mp °C. |
|---|---|---|---|---|---|---|
| 28 | 2-thienyl | Cl | $OCH_3$ | $CH_3$ | H | 66–68 |

EXAMPLE 29
Preparation of 6-cyclohexyl-3-methoxy-4-methylpyridazine

A mixture of 4-methyl-3-methoxy-6-phenylpyridazine (5.0 g), platinum dioxide (400 mg) and trifluoroacetic acid (20 mL) is shaken in a Parr apparatus until hydrogen uptake ceases. The catalyst is removed by filtration, and the cake is washed with additional acid. The filtrate is poured into water and adjusted to basic ph with sodium hydroxide. The solids which precipitate are collected, washed with water, and dried to give 4.6 g (90%) of product which, on crystallization from pentane, gives an analytically pure product having a melting point of 72°–74° C. 3-Methoxy-4-methyl-6-(4-methylcyclohexyl)pyridazine, melting point 84°–98° C. (Example 29a), and 3-cyclohexyl-6-methoxy-4,5-dimethylpyridazine, melting point 99°–101° C. (Example 29b) are also made by the above procedure using the corresponding 6-phenylpyridazine.

EXAMPLE 30
Preparation of 3-amino-4-methyl-6-phenylpyridazine

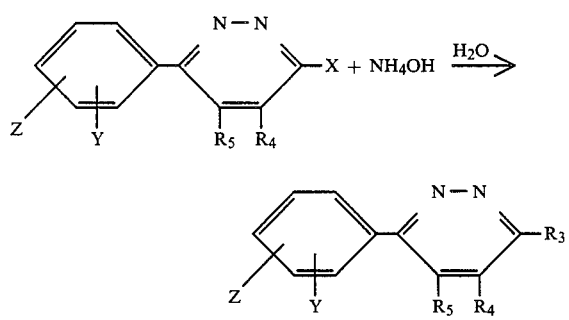

A mixture of 3-fluoro-4-methyl-6-phenylpyridazine (1.0 g) and 50 mL of 28% aqueous $NH_4OH$ is heated in a pressure bottle to 95°–100° C. The reaction mixture is cooled and thereafter extracted with $CH_2Cl_2$. The organic materials are then extracted with 10% aqueous HCl. The acid phase is washed with $CH_2Cl_2$, cooled and basified with caustic. The resulting mixture is extracted several times with $CH_2Cl_2$. The organic extracts are then combined and dried with $MgSO_4$ and the remaining liquid is concentrated to give 550 mg (56%) crude product as a yellow solid. Recrystallization from EtOH gives an analytically pure material melting at 132°–134° C.

Following the above procedures, but substituting the appropriate 3-halo-5-substituted-6-(substituted)phenylpyridazine for 3-fluoro-4-methyl-6-phenylpyridazine, yields the following compound:

| Example | X | Y | Z | $R_3$ | $R_4$ | $R_5$ | mp° C. |
|---|---|---|---|---|---|---|---|
| 31 | F | H | 3-$CF_3$ | $NH_2$ | H | $CH_3$ | 173–175 |

EXAMPLE 32
Preparation of substituted and unsubstituted pyridazines

Preparation of the compounds having the structure illustrated below are prepared according to processes described in U.S. Pat. No. 4,112,095, issued Sept. 5, 1978, or in a publication of J. D. Albright et al., *J. Heterocyclic Chem.* 1978, 15, 881.

| Example | Y | Z | $R_3$ | $R_4$ | $R_5$ | mp °C. |
|---|---|---|---|---|---|---|
| 33 | H | 3-$CF_3$ | Cl | $CH_3$ | H | 123–126 |
| 34 | H | H | F | $CH_3$ | H | 122–124.5 |
| 35 | H | 4-F | Cl | $CH_3$ | H | 177–178 |
| 36 | H | 3-$OCHF_2$ | Cl | $CH_3$ | H | 59–61 |
| 37 | 4-Cl | 2-Cl | Cl | $CH_3$ | H | 104–106 |
| 37a | H | 2-$OCH_3$ | Cl | $CH_3$ | H | red oil |
| 37b | H | H | Cl | $CH_3$ | $CH_3$ | 166–168 |
| 37c | 3-$CH_3$ | 5-$CH_3$ | Cl | $CH_3$ | H | 120–122 |
| 37d | H | H | I | $CH_3$ | H | 126–127 |
| 37e | H | 2-Br | Cl | $CH_3$ | H | 110–112 |

EXAMPLE 38
Preparation of 3-dimethylamino-4,5-dimethyl-6-phenylpyridazine

A 1.5 g sample of 3-chloro-4,5-dimethyl-6-phenylpyridazine is placed in a 6 oz. glass pressure bottle and covered with 15 mL of condensed dimethylamine. To this mixture is added several drops of HI. The bottle is then closed, fitted with a pressure guage and heated for 50 hours at 90°–100° C. and 85–100 psig pressure. The mixture is cooled, excess dimethylamine is evaporated, and the residue partitioned between $CH_2Cl_2$ and water. The organic layer is separated and dried over $MgSO_4$. Removal of the drying agent and concentration of the solvent in vacuo leaves a brown solid (1.7 g). The crude solid is boiled in cyclohexane, filtered; the filtrate diluted with hexane and chilled. The product (0.7 g) is isolated as a mustard-colored solid which melts at 86°–89° C.

Using the appropriate halogenated pyridazine and amine, the aminopyridazines listed in Table III below can be prepared in the same manner as described above. The products prepared by this procedure can be purified by column chromatography on silica gel.

TABLE III

PREPARATION OF AMINOPYRIDAZINES HAVING THE STRUCTURE:

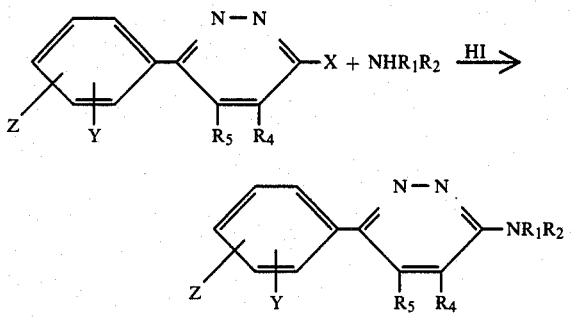

| Example | X | Y | Z | $R_1$ | $R_2$ | $R_4$ | $R_5$ | mp °C. |
|---|---|---|---|---|---|---|---|---|
| 39 | Cl | H | 3-$CF_3$ | $CH_3$ | $CH_3$ | $CH_3$ | H | 60–63 |
| 40 | Cl | H | 3-$CF_3$ | H | $NH_2$ | $CH_3$ | H | 147–148 |
| 41 | Cl | H | 3-$CF_3$ | H | $NHCO_2C_2H_5$ | $CH_3$ | H | 150–152 |
| 42 | Cl | H | H | $CH_3$ | $CH_3$ | $CH_3$ | H | Brown oil |
| 43 | Cl | H | H | H | $CH_3$ | $CH_3$ | H | 88–90 |
| 44 | Cl | H | 3-Cl | $CH_3$ | $CH_3$ | $CH_3$ | H | Gold oil |
| 45 | Cl | H | H | H | $C_2H_5$ | $CH_3$ | H | Brown oil |
| 46 | Cl | H | 3-$OCH_3$ | $CH_3$ | $CH_3$ | $CH_3$ | H | Brown oil |
| 47 | Cl | H | 3-$CF_3$ | H | $NHCO_2C_2H_5$ | H | H | 168–170 |
| 48 | Cl | H | 3-$CF_3$ | H | $NH_2$ | H | H | 155–160 |
| 49 | Cl | H | 2-$CH_3$ | $CH_3$ | $CH_3$ | $CH_3$ | H | 107–111 |
| 50 | Cl | H | H | H | $NHCO_2C_2H_5$ | $CH_3$ | H | 172–176 |
| 50a | Cl | H | H | $OCH_3$ | $CH_3$ | $CH_3$ | H | 60–63 |
| 50b | Cl | 2-F | H | $CH_3$ | $CH_3$ | $CH_3$ | H | Yellow oil |
| 50c | Cl | H | 3-$OCHF_2$ | $CH_3$ | $CH_3$ | $CH_3$ | H | 61–63 |
| 50d | Cl | H | H | $CH_3$ | $CH_3$ | $CH_3$ | H | Yellow oil |

EXAMPLE 51

Preparation of 3-dimethylamino-4-methyl-6-(2-thienyl)pyridazine

The above-named compound is prepared in the same manner as described for the aminopyridazines of Example 38, excepting that 3-chloro-4-methyl-6-(2-thienyl)pyridazine is substituted for 3-chloro-4,5-dimethyl-6-phenylpyridazine. The product obtained has a melting point of 50°–52° C. 3-(Dimethylamino)-4-methyl-6-(3-thienyl)pyridazine, a red oil, (Example 51a) is made in the same manner as described above for the 2-thienyl derivative.

EXAMPLE 52

Preparation of 5-methyl-3($\alpha,\alpha,\alpha$-trifluoro-m-tolyl)pyridazine

To 3-chloro-4-methyl-6-($\alpha,\alpha,\alpha$-trifluoro-m-tolyl)pyridazine (7 g) is added 10% palladium on carbon catalyst (0.7 g) and 300 mL of MeOH containing 30 mL of concentrated $NH_4OH$. The mixture is shaken with $H_2$ until the uptake of $H_2$ ceases. The mixture is filtered to remove catalyst and concentrated in vacuo and then diluted with $CH_2Cl_2/H_2O$. The organic phase is washed with water and dried over $MgSO_4$ to yield a solid which, on recrystallization from $Et_2O$, gives 4.8 g (78%) of an off-white solid with a melting point of 114°–116° C.

EXAMPLE 53

Preparation of 3-(m-chlorophenyl)-5-methylpyridazine

3-Chloro-6-(m-chlorophenyl)-4-methylpyridazine (7.2 g) is partially dissolved in 150 mL of acetic acid containing 1.5 g of 10% palladium on carbon. The mixture is shaken on the Parr hydrogenator until the theoretical amount of hydrogen is consumed.

The catalyst is recovered by filtration and the acetic acid evaporated on the rotary evaporator. The remaining oil is slurried in water, basified using $NH_4OH$, and the resulting solid isolated by filtration and vacuum dried to give 5.0 g (82%) of product with a melting point of 100°–101.5° C.

In a similar manner, the appropriate chloropyridazines are dehalogenated by the above procedure or the procedure of Example 52 to give the compounds reported in Table IV below.

Dehalogenation of 3-chloro-4-methyl-6-(3-pyridyl)pyridazine by the above procedure yields 5-methyl-3-(3-pyridyl)pyridazine having a melting point of 117°–118° C.

TABLE IV

PREPARATION OF PYRIDAZINES HAVING THE STRUCTURE:

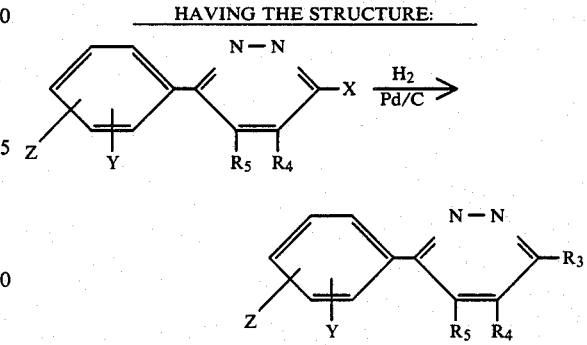

| Example | X | Y | Z | $R_3$ | $R_4$ | $R_5$ | mp °C. |
|---|---|---|---|---|---|---|---|
| 54 | Cl | H | H | H | $CH_3$ | H | 94–96 |
| 55 | Cl | H | 3-$CF_3$ | H | $CH_3$ | H | 123–126 |
| 56 | Cl | H | 3-F | H | $CH_3$ | H | 90–92 |
| 57 | Cl | H | 3-$CH_3$ | H | $CH_3$ | H | 68–69 |
| 58 | Cl | H | 3-$CF_3$ | H | H | $CH_3$ | 82–84 |
| 59 | Cl | H | H | H | $CH_3$ | $CH_3$ | 86–88 |
| 60 | Cl | H | 2-$CH_3$ | H | $CH_3$ | H | 52–54 |
| 60a | Cl | H | 3-$OCHF_2$ | H | $CH_3$ | H | 44–46 |

EXAMPLE 61

Preparation of 5-methyl-3-phenylpyridazine-1-oxide

To a solution of 5-methyl-3-phenylpyridazine (2.0 g) in 40 mL of $CHCl_3$ is added m-chloroperbenzoic acid (2.9 g, 80% pure). The solution is permitted to stand at room temperature until the reaction is complete. The precipitate which forms during the reaction period is removed by filtration, and the filtrate diluted with ether. The ether solution is then washed sequentially with 10% aqueous sodium sulfite, saturated sodium bicarbonate, and saturated brine. The washed liquid is dried over $MgSO_4$ and then concentrated in vacuo to give 1.6 g (73%) of a pale yellow crystalline solid having a melting point of 112°–114° C.

The N-oxides reported in Table V below are prepared as described above using the appropriate pyridazine.

TABLE V
PREPARATION OF PYRIDAZINE-N—OXIDES HAVING THE STRUCTURE:

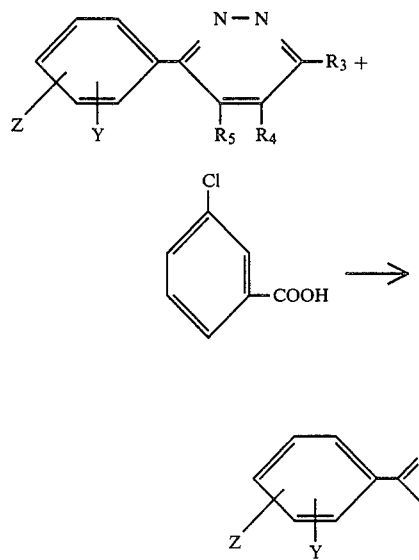

| Example | Y | Z | $R_3$ | $R_4$ | $R_5$ | mp °C. |
|---------|---|---|-------|-------|-------|--------|
| 62 | H | H | $OCH_3$ | $CH_3$ | H | 116–117 |
| 63 | H | 3-$CF_3$ | H | $CH_3$ | H | 130–132 |
| 64 | H | 3-$CF_3$ | H | H | $CH_3$ | 102–105 |
| 65 | H | 3-$CH_3$ | H | $CH_3$ | H | 87–89 |
| 65a | H | 3-Cl | H | $CH_3$ | H | 134.5–136 |
| 65b | H | 3-$OCF_3$ | H | $CH_3$ | H | — |

EXAMPLE 66

Postemergence Herbicidal activity

The postemergence herbicidal activity of test compounds is demonstrated by the following tests wherein a variety of monocotyledonous and dicotyledonous plants are treated with test compounds dispersed in aqueous acetone mixtures. In the tests, seedling plants are grown in separate cups for about two weeks. The test compounds are dispersed in 50/50 acetone/water mixtures containing 0.5% TWEEN ®20, a polyoxyethylene sorbitan monolaurate surfactant of Atlas Chemical Industries, in sufficient quantity to provide the equivalent of about 0.25 kg to 8.0 kg per hectare of active compound when applied to the plants through a spray nozzle operating at 2.81 kg/cm² pressure for a predetermined time. After spraying, the plants are placed on greenhouse benches and are cared for in the usual manner commensurate with conventional greenhouse practices. Two weeks after treatment, the seedling plants are examined and rated according to the rating system provided below. The data obtained are reported in Table VI below, wherein it can be seen that these compounds effectively control broadleaf weeds and grasses.

| RATING SYSTEM | |
|---|---|
| Rating: | Percent Control (Compared to Check) |
| 9 - Complete kill | 100 |
| 8 - Approaching complete kill | 91–99 |
| 7 - Good herbicidal effect | 80–90 |
| 6 - Herbicidal effect | 65–79 |
| 5 - Definite injury | 45–64 |
| 4 - Injury | 30–44 |
| 3 - Moderate effect | 10–29 |
| 2 - Slight effect | 6–15 |
| 1 - Trace effect | 1–5 |
| 0 - No effect | 0 |

The above rating scale is based upon a visual observation of plant stand, vigor, malformation, size, chlorosis, and overall plant appearance as compared with a control.

| PLANT SPECIES USED FOR EVALUATION | |
|---|---|
| Blackgrass | (*Alopecurus myosuroides*) |
| Crabgrass | (*Digitaria sanguinalis*) |
| Wild Oat | (*Avena fatua*) |
| Lambsquarters | (*Chenopodium album*) |
| Morningglory | (*Ipomea spp.*) |
| Wild Mustard | (*Brassica kaber*) |
| Redroot Pigweek | (*Amaranthus retroflexus*) |
| Ragweed | (*Ambrosia artemisiifolia*) |
| Velvetleaf | (*Abutilon theoprasti*) |
| Field Corn | (*Zea mays*) |
| Cotton | (*Gossypium hirsutum*) |
| Soybean | (*Glycine max*) |
| Sunflower | (*Helianthus anndus*) |
| Barley | (*Hordeum vulgare*) |
| Wheat | (*Triticum alstivum*) |

TABLE VI

POST-EMERGENCE TESTS - RATES IN KG/HA

| Compound of Example No. | RATE | BLACK GRASS | LARGE CRAB | GREEN FOX | WILD OATS | LAMBS QTRS | MRNGL RY SP | WILD MUSTD | RED PIGWED | RAG-WEED | VELVET-LEAF | CORN FIELD | COTTON | SOYBEAN AD | SUNFLR XXX | BAR-LEY | S WHEAT ER |
|---|---|---|---|---|---|---|---|---|---|---|---|---|---|---|---|---|---|
| 1 | 5.000 | 9.0 | 9.0 | 9.0 | 9.0 | 9.0 | 9.0 | 9.0 | 9.0 | 9.0 | 9.0 | 7.9 | 9.0 | 9.0 | 9.0 | 9.0 | 9.0 |
|  | 4.000 | 9.0 |  | 9.0 | 9.0 | 9.0 | 9.0 | 9.0 | 9.0 | 9.0 | 9.0 | 4.5 | 8.8 | 9.0 | 9.0 |  | 9.0 |
|  | 2.000 | 9.0 |  | 8.8 | 8.9 | 9.0 | 8.7 | 9.0 | 9.0 | 9.0 | 9.0 | 3.0 | 8.5 | 8.9 | 9.0 |  | 8.3 |
|  | 1.000 | 9.0 |  | 8.4 | 8.3 | 9.0 | 8.3 | 8.8 | 9.0 | 9.0 | 9.0 | 2.3 | 8.5 | 8.9 | 8.0 |  | 7.7 |
|  | .500 | 8.8 |  | 6.4 | 7.3 | 9.0 | 7.0 | 8.3 | 7.0 | 6.7 | 8.3 | 1.5 | 7.8 | 8.1 | 7.0 |  | 5.5 |
|  | .250 | 7.0 |  | 4.3 | 5.5 | 9.0 | 3.8 | 6.4 | 6.0 | 4.5 | 5.5 | 0.3 | 6.2 | 6.3 | 4.0 |  | 3.2 |
|  | .125 | 2.5 |  | 2.6 | 4.0 | 9.0 | 0.5 | 4.0 | 0.0 | 1.3 | 3.2 | 0.0 | 4.0 | 3.0 | 1.0 |  | 2.8 |
|  | .063 | 0.0 |  | 1.3 | 2.0 | 9.0 | 0.0 | 6.0 | 6.0 | 6.0 | 7.0 | 5.5 | 2.7 | 8.0 | 9.0 |  | 4.5 |
| 2 | 4.000 | 4.5 | 9.0 | 9.0 | 7.5 | 5.5 | 8.3 | 6.0 | 6.0 | 6.0 | 4.3 | 2.0 | 3.0 | 8.0 | 5.0 | 4.0 | 3.7 |
|  | 2.000 | 0.0 |  | 4.5 | 6.5 | 3.0 | 7.5 | 4.5 | 3.5 | 6.7 | 3.8 | 0.7 | 1.7 | 8.0 | 4.5 | 6.0 | 3.3 |
|  | 1.000 | 0.0 | 0.0 | 3.0 | 5.3 | 0.0 | 3.7 | 3.7 | 0.7 | 1.5 | 0.7 | 1.0 | 0.7 | 6.5 | 1.0 | 2.0 | 1.3 |
|  | .500 | 0.0 |  | 3.0 | 4.0 | 0.0 | 3.0 | 0.0 | 0.0 | 0.0 | 0.0 | 0.0 | 0.7 | 4.5 |  | 0.0 | 0.7 |
|  | .250 | 0.0 |  | 0.5 | 2.5 |  | 0.0 | 0.0 | 0.0 | 0.0 | 0.0 | 0.0 |  |  |  |  |  |
| 3 | 8.000 | 8.0 | 9.0 | 9.0 | 8.0 | 9.0 | 9.0 | 9.0 | 9.0 | 7.0 | 7.0 | 0.0 | 9.0 |  | 9.0 | 7.0 |  |
|  | 4.000 | 8.0 |  |  | 8.0 | 9.0 | 7.0 | 9.0 |  | 0.0 | 9.0 | 0.0 | 7.0 |  | 9.0 | 7.0 |  |
|  | 2.000 | 7.0 |  |  | 0.0 | 9.0 | 0.0 | 9.0 |  | 0.0 | 9.0 | 0.0 | 7.0 |  | 8.0 | 7.0 |  |
|  | 1.000 | 8.0 |  |  | 7.0 |  | 9.0 | 9.0 |  | 0.0 | 9.0 |  |  |  |  |  |  |
| 4 | 8.000 | 9.0 | 9.0 | 9.0 | 9.0 |  | 9.0 | 9.0 | 9.0 | 9.0 | 9.0 | 9.0 | 9.0 |  | 9.0 | 9.0 | 9.0 |
|  | 4.000 | 9.0 |  | 7.0 | 9.0 |  | 9.0 | 9.0 | 8.0 | 9.0 | 9.0 | 3.0 | 4.0 | 9.0 | 5.0 |  | 8.0 |
|  | 2.000 | 9.0 |  | 5.0 | 9.0 |  | 9.0 | 9.0 | 7.0 | 9.0 | 9.0 | 3.5 | 5.5 | 9.0 | 8.5 | 8.0 | 6.0 |
|  | 1.000 | 8.0 |  | 2.0 | 7.5 |  | 7.0 | 7.5 | 2.0 | 7.0 | 8.3 | 1.0 | 5.5 | 9.0 | 7.0 | 6.0 | 3.0 |
|  | .500 | 4.5 |  | 1.0 | 5.5 |  | 5.5 | 8.5 | 0.0 | 6.5 | 8.3 | 0.0 | 4.5 | 7.0 | 5.5 | 5.0 |  |
| 5 | 5.000 |  | 9.0 | 9.0 | 9.0 | 9.0 | 9.0 | 9.0 |  | 9.0 | 9.0 | 0.0 | 9.0 | 9.0 |  |  |  |
|  | 4.000 |  |  | 9.0 | 9.0 | 9.0 | 9.0 | 9.0 |  | 0.0 | 9.0 | 3.0 | 9.0 | 9.0 |  |  |  |
|  | 2.000 |  |  | 9.0 | 8.0 | 9.0 | 9.0 | 9.0 |  | 0.0 | 8.0 | 3.0 | 9.0 | 9.0 |  |  |  |
|  | 1.000 |  |  | 9.0 | 7.0 |  | 9.0 | 9.0 |  | 0.0 | 6.0 | 2.0 | 8.0 | 9.0 |  |  |  |
|  | .500 |  |  | 7.0 | 5.0 |  | 5.0 | 5.0 |  |  | 9.0 | 2.0 | 8.0 |  |  |  |  |
| 6 | 8.000 |  | 9.0 | 9.0 | 9.0 |  | 9.0 | 9.0 |  | 9.0 | 9.0 | 3.0 | 9.0 | 8.0 |  |  |  |
|  | 4.000 |  |  | 9.0 | 8.0 |  | 7.0 | 9.0 |  |  |  | 3.0 | 9.0 | 8.0 |  |  |  |
|  | 2.000 |  |  | 5.0 | 5.0 |  | 5.0 | 9.0 |  |  |  | 1.0 | 5.0 | 7.0 |  |  |  |
|  | 1.000 |  |  | 1.0 | 4.0 |  | 1.0 | 5.0 |  |  |  | 0.0 | 1.0 | 7.0 |  |  |  |
| 7 | 8.000 |  | 9.0 | 9.0 | 9.0 |  | 9.0 | 9.0 |  | 9.0 | 9.0 | 5.0 | 9.0 | 8.0 |  |  |  |
|  | 4.000 |  |  | 9.0 | 7.0 |  | 3.0 | 9.0 |  |  |  | 2.0 | 9.0 | 7.0 |  |  |  |
|  | 2.000 |  |  | 9.0 | 1.0 |  | 2.0 | 9.0 |  |  |  | 1.0 | 7.0 | 6.0 |  |  |  |
|  | 1.000 |  |  | 9.0 | 1.0 |  | 1.0 | 3.0 |  |  |  | 0.0 | 5.0 | 5.0 |  |  |  |
|  | .500 |  |  | 8.0 | 0.0 |  | 0.0 | 7.0 |  |  |  | 1.0 | 3.5 | 3.0 |  |  |  |
| 8 | 4.000 |  |  | 6.0 | 7.0 |  | 7.5 | 9.0 |  |  |  | 0.0 | 2.0 | 5.0 |  |  |  |
|  | 2.000 |  |  | 3.5 | 2.0 |  | 6.0 | 7.0 |  |  |  | 0.0 | 1.0 | 3.0 |  |  |  |
|  | 1.000 |  |  | 9.0 | 1.0 |  | 9.0 | 4.5 |  |  |  | 0.0 |  | 4.0 |  |  |  |
| 9 | 8.000 |  | 9.0 | 9.0 | 9.0 |  | 9.0 | 9.0 |  | 9.0 | 9.0 | 3.0 | 9.0 | 8.0 |  |  |  |
|  | 4.000 |  |  | 8.0 | 8.0 |  | 6.0 | 9.0 |  |  |  | 2.0 | 9.0 | 9.0 |  |  |  |
|  | 2.000 |  |  | 7.0 | 5.0 |  | 9.0 | 8.0 |  |  |  | 1.0 | 8.0 | 5.0 |  |  |  |
|  | 1.000 |  |  | 1.0 | 4.0 |  | 2.0 | 7.0 |  |  |  | 0.0 |  | 5.0 |  |  |  |
|  | .500 |  |  | 0.0 | 1.0 |  | 9.0 | 8.0 |  |  |  | 0.0 |  | 4.0 |  |  |  |
| 10 | 8.000 |  | 9.0 | 9.0 | 9.0 |  | 9.0 | 9.0 |  | 9.0 | 9.0 | 2.0 | 7.0 | 9.0 |  |  |  |
|  | 4.000 |  |  | 8.0 | 5.0 |  | 9.0 | 9.0 |  |  |  | 2.0 |  | 9.0 |  |  |  |
|  | 2.000 |  |  | 5.0 | 4.0 |  | 7.0 | 9.0 |  |  |  |  |  |  |  |  |  |

TABLE VI-continued

POST-EMERGENCE TESTS - RATES IN KG/HA

| Compound of Example No. | RATE | BLACK GRASS | LARGE CRAB | GREEN FOX | WILD OATS | LAMBS QTRS | MRNGL RY SP | WILD MUSTD | RED PIGWED | RAG-WEED | VELVET-LEAF | CORN FIELD | COTTON | SOYBEAN AD | SUNFLR XXX | BAR-LEY | S WHEAT ER |
|---|---|---|---|---|---|---|---|---|---|---|---|---|---|---|---|---|---|
| 11 | 1.000 | | | 3.0 | 1.0 | | 5.0 | 8.0 | | | | 1.0 | 5.0 | 5.0 | | | |
| | 4.000 | | | 9.0 | 9.0 | | 9.0 | 9.0 | | | | 8.0 | 9.0 | 9.0 | | | |
| | 2.000 | | | 5.0 | 7.0 | | 9.0 | 9.0 | | | | 7.0 | 9.0 | 9.0 | | | |
| | 1.000 | | | 1.0 | 6.0 | | 8.0 | 9.0 | | | | 5.0 | 9.0 | 9.0 | | | |
| | .500 | | | 1.0 | 5.0 | | 7.0 | 9.0 | | | | 3.0 | 9.0 | 9.0 | | | |
| | .250 | | | 0.0 | 3.0 | | 3.0 | 2.0 | | | | 3.0 | 8.0 | 9.0 | | | |
| 16 | 8.000 | | 9.0 | 9.0 | 9.0 | 9.0 | 9.0 | 9.0 | 9.0 | 9.0 | 9.0 | | | | | | |
| | 4.000 | 0.0 | | | 0.0 | | | | | 7.0 | 9.0 | | | | | 0.0 | |
| | 2.000 | 0.0 | | | | 9.0 | 2.0 | 9.0 | | 0.0 | 9.0 | 0.0 | 8.0 | | 0.0 | 0.0 | |
| | 1.000 | 0.0 | | | | 6.0 | 0.0 | 9.0 | | 0.0 | 8.5 | 0.0 | 0.0 | | 0.0 | 0.0 | |
| | .500 | | | | | 0.0 | 0.0 | 9.0 | | 0.0 | 7.0 | 0.0 | 0.0 | | 0.0 | 0.0 | |
| | .250 | | | | | | 0.0 | 2.0 | | | 2.0 | 0.0 | 0.0 | | | | |
| 18 | 4.000 | | | 5.0 | 8.0 | | 5.0 | 9.0 | | | | 3.0 | 1.0 | 9.0 | | | |
| | 2.000 | | | 4.0 | 1.0 | | 1.0 | 5.0 | | | | 1.0 | 1.0 | 7.0 | | | |
| | 1.000 | | | 4.0 | 0.0 | | 0.0 | 1.0 | | | | 0.0 | 0.0 | 2.0 | | | |
| 19 | 8.000 | | 9.0 | 9.0 | 9.0 | | 9.0 | 9.0 | | 9.0 | 9.0 | 9.0 | 9.0 | 9.0 | | | |
| | 4.000 | | | 9.0 | 9.0 | | 9.0 | 9.0 | | | | 5.0 | 9.0 | 9.0 | | | |
| | 2.000 | | | 7.0 | 9.0 | | 9.0 | 9.0 | | | | 2.0 | 9.0 | 9.0 | | | |
| | 1.000 | | | 5.0 | 7.0 | | 8.0 | 9.0 | | | | 1.0 | 9.0 | 2.0 | | | |
| | .500 | | | 1.0 | 1.0 | | 5.0 | 8.0 | | | | 0.0 | 9.0 | 1.0 | | | |
| | .250 | | | 0.0 | 0.0 | | 0.0 | 1.0 | | | | 0.0 | 9.0 | 0.0 | | | |
| 21 | 8.000 | | 9.0 | 9.0 | 9.0 | | 9.0 | 9.0 | | 9.0 | 9.0 | 0.0 | 9.0 | 9.0 | | | |
| | 4.000 | | | 9.0 | 9.0 | | 9.0 | 9.0 | | | | 0.0 | 8.0 | 8.0 | | | |
| | 2.000 | | | 8.0 | 1.0 | | 8.0 | 9.0 | | | | 0.0 | 5.0 | 3.0 | | | |
| | 1.000 | | | 1.0 | 0.0 | | 1.0 | 9.0 | | | | 0.0 | 1.0 | 1.0 | | | |
| | .500 | | | 0.0 | 0.0 | | 0.0 | 1.0 | | | | 0.0 | 0.0 | 0.0 | | | |
| 22 | 8.000 | | 9.0 | 9.0 | 9.0 | | 9.0 | 9.0 | | 9.0 | 9.0 | 0.0 | 8.0 | 9.0 | | | |
| | 4.000 | | | 5.0 | 9.0 | | 9.0 | 9.0 | | | | 0.0 | 5.0 | 9.0 | | | |
| | 2.000 | | | 3.0 | 2.0 | | 5.0 | 9.0 | | | | 0.0 | 5.0 | 7.0 | | | |
| | 1.000 | | | 0.0 | 0.0 | | 2.0 | 8.0 | | | | 0.0 | 2.0 | 5.0 | | | |
| | .500 | | | 0.0 | 0.0 | | 1.0 | 1.0 | | | | 0.0 | 0.0 | 1.0 | | | |
| 24 | 8.000 | | 9.0 | 9.0 | 9.0 | | 9.0 | 9.0 | | 9.0 | 9.0 | 0.0 | 9.0 | 9.0 | | | |
| | 4.000 | | | 3.0 | 7.0 | | 9.0 | 9.0 | | | | 0.0 | 9.0 | 9.0 | | | |
| | 2.000 | | | 0.0 | 1.0 | | 7.0 | 9.0 | | | | 0.0 | 9.0 | 1.0 | | | |
| | 1.000 | | | 0.0 | 0.0 | | 1.0 | 9.0 | | | | 0.0 | 8.0 | 1.0 | | | |
| | .500 | | | 0.0 | 0.0 | | 1.0 | 0.0 | | | | 0.0 | 7.0 | 0.0 | | | |
| 27 | 8.000 | | 9.0 | 9.0 | 9.0 | | 9.0 | 9.0 | | 9.0 | 9.0 | 0.0 | 9.0 | 9.0 | | | |
| | 4.000 | | | 9.0 | 9.0 | | 9.0 | 9.0 | | | | 3.0 | 9.0 | 9.0 | | | |
| | 2.000 | | | 9.0 | 7.0 | | 9.0 | 9.0 | | | | 2.0 | 9.0 | 9.0 | | | |
| | 1.000 | | | 7.0 | 5.0 | | 5.0 | 5.0 | | | | 0.0 | 8.0 | 7.0 | | | |
| | .500 | | | 5.0 | 5.0 | | 1.0 | 9.0 | | | | 0.0 | 5.0 | 6.0 | | | |
| | .250 | | | 0.0 | 1.0 | | 0.0 | 9.0 | | | | | | | | | |
| | .125 | | | 0.0 | 0.0 | | 0.0 | 5.0 | | | | | | | | | |
| 28 | 8.000 | | 9.0 | 9.0 | 9.0 | | 9.0 | 9.0 | | 9.0 | 9.0 | 1.0 | 9.0 | 9.0 | | | |
| | 4.000 | | | 7.0 | 8.0 | | 2.0 | 9.0 | | | | 1.0 | 9.0 | 9.0 | | | |
| | 2.000 | | | 1.0 | 7.0 | | 1.0 | 9.0 | | | | 0.0 | 9.0 | 4.0 | | | |
| | 1.000 | | | 0.0 | 5.0 | | 0.0 | 5.0 | | | | 0.0 | 9.0 | 3.0 | | | |
| | .500 | | | 0.0 | 1.0 | | 0.0 | 1.0 | | | | 0.0 | 9.0 | 2.0 | | | |
| | .250 | | | 0.0 | 0.0 | | 0.0 | 0.0 | | | | 0.0 | 8.0 | | | | |

TABLE VI-continued

POST-EMERGENCE TESTS - RATES IN KG/HA

| Compound of Example No. | RATE | BLACK GRASS | LARGE CRAB | GREEN FOX | WILD OATS | LAMBS QTRS | MRNGL RY SP | WILD MUSTD | RED PIGWED | RAG-WEED | VELVET-LEAF | CORN FIELD | COTTON | SOYBEAN AD | SUNFLR XXX | BAR-LEY | S WHEAT ER |
|---|---|---|---|---|---|---|---|---|---|---|---|---|---|---|---|---|---|
| 29 | .125 | | | 0.0 | 0.0 | | 0.0 | 0.0 | | | | 0.0 | 5.0 | 0.0 | | | |
| | 8.000 | | 9.0 | 9.0 | 9.0 | | 9.0 | 9.0 | | 9.0 | 9.0 | 3.0 | 9.0 | 9.0 | | | |
| | 4.000 | | | 9.0 | 5.0 | | 9.0 | 9.0 | | | | 3.0 | 9.0 | 8.0 | | | |
| | 2.000 | | | 9.0 | 1.0 | | 5.0 | 5.0 | | | | 1.0 | 9.0 | 3.0 | | | |
| | 1.000 | | | 5.0 | 0.0 | | 1.0 | 1.0 | | | | 0.0 | 9.0 | 2.0 | | | |
| | .500 | | | 1.0 | 0.0 | | 0.0 | 0.0 | | | | | | | | | |
| 52 | 8.000 | | 9.0 | 9.0 | 9.0 | | 9.0 | 9.0 | | 9.0 | 9.0 | | | | | | |
| | 4.000 | | | 7.0 | 0.0 | | | 7.0 | | | | 5.0 | 4.0 | | | | |
| | 2.000 | | | 5.0 | 0.0 | | 9.0 | 2.0 | | | | 5.0 | 1.0 | | | | |
| | 1.000 | | | 1.0 | 0.0 | | 9.0 | 2.0 | | | | 5.0 | 0.0 | | | | |
| | .500 | | | 0.0 | 0.0 | | 5.0 | 2.0 | | | | 2.0 | 0.0 | | | | |
| 54 | 8.000 | | 7.0 | 5.0 | 9.0 | | 9.0 | 9.0 | | 9.0 | 9.0 | 2.0 | 3.0 | 3.0 | | | |
| | 4.000 | | | 7.0 | 0.0 | | 2.0 | 9.0 | | | | 2.0 | 3.0 | 3.0 | | | |
| | 2.000 | | | 5.0 | 0.0 | | 2.0 | 8.0 | | | | 1.0 | 3.0 | 3.0 | | | |
| | 1.000 | | | 4.0 | 0.0 | | 1.0 | 1.0 | | | | | | | | | |
| 62 | 8.000 | | 9.0 | 9.0 | 9.0 | | 9.0 | 9.0 | | 9.0 | 9.0 | 3.0 | 3.0 | | | | |
| | 4.000 | | | 8.0 | 5.0 | | 9.0 | 9.0 | | | | 3.0 | | | | | |
| | 2.000 | | | 8.0 | 5.0 | | 9.0 | 7.0 | | | | 1.0 | 2.0 | | | | |
| | 1.000 | | | 5.0 | 0.0 | | 4.0 | 5.0 | | | | | | | | | |
| 24a | 5.000 | 0.0 | 0.0 | 1.0 | 0.0 | 0.0 | 3.0 | 9.0 | 8.0 | 5.0 | 5.0 | 0.0 | 0.0 | | 2.0 | 0.0 | |
| | 4.000 | | | | | | 9.0 | 9.0 | | 0.0 | 4.0 | | | | | | |
| 24b | 8.000 | 0.0 | 7.0 | 9.0 | 8.0 | 9.0 | 5.0 | 9.0 | 9.0 | 6.0 | 8.5 | 2.0 | 3.0 | | 0.0 | 0.0 | |
| | 4.000 | | | | 0.0 | | 9.0 | 9.0 | | 0.0 | 3.5 | | | | | | |
| 37b | 8.000 | | 9.0 | 9.0 | 9.0 | | 5.0 | 9.0 | | 9.0 | 9.0 | | | | | | |
| | 4.000 | | | 9.0 | 9.0 | | 9.0 | 9.0 | | | | 3.0 | 9.0 | 9.0 | | | |
| | 2.000 | | | 9.0 | 9.0 | | 9.0 | 9.0 | | | | 3.0 | 7.0 | 8.0 | | | |
| | 1.000 | | | 8.0 | 5.0 | | 5.0 | 8.0 | | | | 1.0 | 5.0 | 5.0 | | | |
| | .500 | | | 5.0 | 1.0 | | 0.0 | 1.0 | | | | 0.0 | 1.0 | 3.0 | | | |
| | .250 | | | 1.0 | 0.0 | | 0.0 | 0.0 | | | | 0.0 | 0.0 | 1.0 | | | |
| | .125 | | | 0.0 | 0.0 | | 0.0 | 0.0 | | | | 0.0 | 0.0 | 0.0 | | | |
| 24c | 5.000 | | 9.0 | 9.0 | 6.0 | | 9.0 | 9.0 | | 0.0 | 9.0 | 3.0 | 2.0 | 9.0 | | | |
| | 4.000 | | | 9.0 | 8.0 | | 9.0 | 9.0 | | | | 1.0 | 1.0 | 9.0 | | | |
| | 2.000 | | | 9.0 | 1.0 | | 1.0 | 9.0 | | | | 0.0 | 0.0 | 3.0 | | | |
| | 1.000 | | | 9.0 | 0.0 | | 0.0 | 9.0 | | | | 0.0 | 0.0 | 1.0 | | | |
| | .500 | | | 7.0 | 0.0 | | 0.0 | 9.0 | | | | 0.0 | 0.0 | | | | |

EXAMPLE 67

Protocol for greenhouse testing of the pyridazines

Preemergence Herbicidal activity:

Seeds of a variety of monocotyledonous and dicotyledonous plants are mixed into 50 mL of soil and planted on top of 200 mL of soil with each species in a separate cup. The cups are then arranged in 30.5 cm×45.7 cm flats prior to chemical treatment. The flats are pre-wetted before spraying to insure even spreading of the herbicide application over the soil. Chemicals to be tested are mixed into 80:20 acetone: $H_2O$ (V/V) and sufficient compound to provide the equivalent of 50.125 to 4 kg/ha of active compound when applied through a spray nozzle at 2.8 kg/cm$^2$ pressure for a predetermined time. After spraying, the treated cups are placed on greenhouse benches, watered, and cared for in accordance with conventional greenhouse procedures. Four to five weeks after treatment, the seedling plants are examined and rated according to a standard rating system.

The plant species and rating are the same as described in Example 66. Data obtained are reported in Table VII below.

TABLE VII

PRE-EMERGENCE TESTS - RATES IN KG/HA

| Compound of Example No. | RATE | BLACK GRASS | LARGE CRAB | GREEN FOX | WILD OATS | LAMBS QTRS | MRNGL RY SP | WILD MUSTD | RED PIGWED | RAG-WEED | VELVET-LEAF | CORN FIELD | COTTON | SOYBEAN AD | SUNFLR XXX | BAR-LEY | S WHEAT ER |
|---|---|---|---|---|---|---|---|---|---|---|---|---|---|---|---|---|---|
| 1 | 5.000 |  | 9.0 | 9.0 | 9.0 | 9.0 | 9.0 | 9.0 | 9.0 | 9.0 | 9.0 | 8.6 | 8.8 | 9.0 |  |  | 5.5 |
|  | 4.000 | 9.0 |  | 9.0 | 9.0 | 9.0 | 9.0 | 9.0 | 9.0 | 9.0 | 9.0 | 7.2 | 8.1 | 9.0 | 2.0 | 8.0 | 9.0 |
|  | 2.000 | 9.0 |  | 9.0 | 9.0 | 9.0 | 8.3 | 9.0 | 9.0 | 9.0 | 9.0 | 3.2 | 5.2 | 8.5 | 0.0 |  | 5.0 |
|  | 1.000 | 9.0 |  | 9.0 | 7.1 | 9.0 | 6.7 | 9.0 | 9.0 | 9.0 | 9.0 | 1.5 | 1.9 | 6.1 | 0.0 | 3.0 | 4.5 |
|  | .500 | 9.0 |  | 8.9 | 4.4 | 9.0 | 4.6 | 9.0 | 9.0 | 9.0 | 9.0 | 0.4 | 1.0 | 4.3 | 0.0 | 0.0 | 1.0 |
|  | .250 |  |  | 4.8 | 0.6 |  | 1.8 | 8.6 |  | 5.0 |  | 0.3 | 0.4 | 2.4 |  | 0.0 | 0.0 |
|  | .125 |  |  |  |  |  | 0.2 |  |  |  |  |  |  |  |  |  | 0.0 |
| 2 | 4.000 | 9.0 |  | 9.0 | 9.0 | 9.0 | 8.5 | 9.0 | 9.0 | 9.0 | 9.0 | 1.0 | 2.0 | 5.0 | 0.0 |  | 9.0 |
|  | 2.000 | 9.0 |  | 9.0 | 6.0 | 9.0 | 4.5 | 9.0 | 9.0 | 7.0 | 9.0 | 1.0 | 0.5 | 2.0 | 0.0 |  | 7.0 |
|  | 1.000 | 7.0 |  | 9.0 | 2.0 | 9.0 | 0.5 | 8.0 | 8.0 | 2.0 | 9.0 | 1.0 | 0.0 | 1.0 | 0.0 |  | 6.0 |
|  | .500 | 4.0 |  | 8.0 | 0.0 | 9.0 | 0.5 | 0.0 | 1.0 | 2.0 | 2.0 | 1.0 | 0.0 | 1.0 | 0.0 |  | 2.0 |
|  | .250 | 2.0 |  | 2.5 | 0.0 | 2.0 | 0.0 |  |  | 1.0 | 2.0 | 0.0 | 0.0 | 1.0 |  |  | 0.0 |
| 3 | 8.000 |  | 9.0 | 9.0 | 9.0 | 9.0 | 0.0 | 9.0 | 9.0 | 3.0 | 9.0 | 0.0 | 0.0 |  |  |  | 0.0 |
|  | 4.000 | 9.0 |  | 9.0 | 9.0 | 9.0 | 7.0 | 9.0 |  | 7.0 | 9.0 | 0.0 | 0.0 |  | 0.0 | 0.0 | 0.0 |
|  | 1.000 | 6.0 |  | 9.0 | 5.0 | 9.0 | 0.0 | 0.0 |  | 0.0 | 0.0 | 0.0 | 0.0 |  | 0.0 | 0.0 | 0.0 |
|  | .500 | 0.0 |  | 0.0 | 0.0 | 9.0 | 0.0 |  |  | 0.0 | 0.0 | 0.0 | 0.0 |  | 0.0 | 0.0 | 0.0 |
|  | .250 | 0.0 |  | 0.0 | 0.0 |  | 0.0 |  |  | 0.0 | 0.0 | 0.0 | 0.0 |  |  |  |  |
| 4 | 8.000 |  | 9.0 | 9.0 | 9.0 |  | 9.0 | 9.0 | 9.0 | 9.0 | 9.0 | 0.0 | 3.0 |  | 5.0 | 8.0 | 8.0 |
|  | 4.000 | 9.0 |  | 9.0 | 9.0 |  | 9.0 | 9.0 | 9.0 | 9.0 | 9.0 | 0.0 | 0.0 |  | 0.0 | 7.0 | 8.0 |
|  | 1.000 | 9.0 |  | 9.0 | 6.0 |  | 9.0 | 9.0 | 8.0 | 7.0 | 2.0 | 0.0 | 0.0 |  | 0.0 | 3.0 | 6.0 |
|  | .500 | 5.0 |  | 7.0 | 8.0 |  | 5.0 | 5.0 |  | 0.0 | 2.0 | 0.0 | 0.0 |  | 0.0 | 0.0 | 5.0 |
|  | .250 | 0.0 |  | 0.0 | 5.0 |  | 0.0 | 2.0 |  | 0.0 | 0.0 |  |  |  |  |  |  |
| 5 | 8.000 |  | 9.0 | 9.0 | 9.0 |  | 9.0 | 9.0 |  | 9.0 | 9.0 | 0.0 | 0.0 |  | 0.0 |  |  |
|  | 5.000 |  | 9.0 | 9.0 | 8.5 |  | 9.0 | 9.0 |  | 9.0 | 9.0 |  |  |  |  |  |  |
|  | 4.000 | 9.0 | 9.0 | 9.0 | 7.0 |  | 9.0 | 9.0 | 9.0 | 9.0 | 9.0 | 2.7 | 5.5 | 7.0 | 3.7 |  | 6.0 |
|  | 2.000 |  |  | 9.0 | 4.5 |  | 7.0 |  |  |  | 9.0 |  | 0.0 | 1.0 |  |  | 7.0 |
|  | 1.000 | 8.0 | 9.0 | 9.0 | 2.0 |  | 0.5 | 9.0 | 8.0 | 2.0 | 9.0 | 0.0 | 2.3 | 0.7 | 0.3 |  | 0.8 |
|  | .500 |  |  | 5.0 | 0.0 |  |  | 1.0 |  |  |  |  | 0.0 | 0.0 |  |  | 0.0 |
| 6 | 8.000 |  | 9.0 | 9.0 | 9.0 |  | 9.0 | 9.0 |  | 9.0 | 9.0 | 2.0 | 2.0 | 9.0 |  |  |  |
|  | 4.000 |  |  | 9.0 | 8.0 |  | 1.0 | 9.0 |  |  |  | 1.0 | 1.0 | 9.0 |  |  |  |
|  | 2.000 |  |  | 9.0 | 1.0 |  | 1.0 | 5.0 |  |  |  | 0.0 | 1.0 | 8.0 |  |  |  |
|  | 1.000 |  |  | 7.0 | 0.0 |  | 0.0 | 2.0 |  |  |  | 0.0 | 0.0 | 5.0 |  |  |  |
| 7 | 8.000 |  | 9.0 | 5.0 | 0.0 |  | 0.0 | 9.0 |  | 0.0 | 9.0 | 0.0 | 0.0 | 4.0 | 2.0 |  | 2.0 |
|  | 4.000 | 9.0 | 9.0 | 9.0 | 6.0 |  | 2.0 | 9.0 | 9.0 | 6.0 | 9.0 | 1.7 | 0.7 | 4.0 | 2.0 |  | 2.0 |
|  | 2.000 |  |  | 9.0 | 4.5 |  | 5.5 | 9.0 |  | 2.0 |  | 2.0 | 1.0 | 3.0 | 0.0 |  | 0.0 |
|  | 1.000 |  | 8.0 | 9.0 | 1.0 |  | 1.0 | 7.0 | 9.0 |  |  | 0.0 | 0.0 | 0.7 |  |  |  |
|  | .500 |  |  | 7.0 | 0.0 |  | 0.0 | 1.0 |  |  |  | 0.0 | 0.0 | 2.0 |  |  |  |
| 8 | 8.000 |  |  | 9.0 | 9.0 |  | 9.0 | 9.0 |  |  |  | 5.0 | 3.0 | 9.0 |  |  |  |
|  | 4.000 |  | 9.0 | 9.0 | 8.0 |  | 5.0 | 9.0 |  |  |  | 4.0 | 2.0 | 9.0 |  |  |  |
|  | 2.000 |  |  | 9.0 | 7.0 |  | 1.0 | 9.0 |  |  |  | 1.0 | 1.0 | 7.0 |  |  |  |
|  | 1.000 |  |  | 7.0 | 1.0 |  | 0.0 | 2.0 |  |  | 9.0 | 0.0 | 0.0 | 5.0 |  |  |  |
|  | .50 |  |  | 1.0 | 0.0 |  | 0.0 |  |  | 9.0 |  |  |  | 4.0 |  |  |  |
| 9 | 8.000 |  | 9.0 | 9.0 | 9.0 |  | 9.0 | 9.0 |  |  |  | 3.0 | 8.0 | 9.0 |  |  |  |
|  | 4.000 |  |  | 9.0 | 9.0 |  | 8.0 | 9.0 |  |  |  | 3.0 | 9.0 | 9.0 |  |  |  |
|  | 2.000 |  |  | 9.0 | 9.0 |  | 7.0 | 9.0 |  |  |  | 2.0 | 6.0 | 8.0 |  |  |  |
|  | 1.000 |  |  | 8.0 | 7.0 |  | 7.0 | 9.0 |  |  |  | 2.0 | 2.0 | 7.0 |  |  |  |
|  | .500 |  |  | 7.0 | 5.0 |  | 5.0 | 9.0 |  |  |  | 0.0 | 2.0 | 5.0 |  |  |  |
|  | .125 |  |  | 9.0 | 9.0 |  | 1.0 | 9.0 |  | 0.0 | 9.0 | 0.0 | 0.0 | 4.0 |  |  |  |
| 10 | 8.000 |  | 9.0 |  |  |  | 9.0 |  |  |  |  |  |  |  |  |  |  |

TABLE VII-continued

PRE-EMERGENCE TESTS - RATES IN KG/HA

| Compound of Example No. | RATE | BLACK GRASS | LARGE CRAB | GREEN FOX | WILD OATS | LAMBS QTRS | MRNGL RY SP | WILD MUSTD | RED PIGWED | RAG-WEED | VELVET-LEAF | CORN FIELD | COTTON | SOYBEAN AD | SUNFLR XXX | BAR-LEY | S WHEAT ER |
|---|---|---|---|---|---|---|---|---|---|---|---|---|---|---|---|---|---|
| | 4.000 | | | 9.0 | 7.0 | | 0.0 | 9.0 | | | | 0.0 | 5.0 | 8.0 | | | |
| | 2.000 | | | 9.0 | 5.0 | | 0.0 | 9.0 | | | | 0.0 | 2.0 | 7.0 | | | |
| | 1.000 | | | 9.0 | 5.0 | | 0.0 | 8.0 | | | | 0.0 | 1.0 | 5.0 | | | |
| | .500 | | | 7.0 | 1.0 | | 0.0 | 5.0 | | | | 0.0 | 0.0 | 2.0 | | | |
| | .250 | | | 1.0 | 0.0 | | 0.0 | 0.0 | | | | 0.0 | 0.0 | 0.0 | | | |
| 11 | 4.000 | | | 9.0 | 9.0 | | 9.0 | 9.0 | | | | 7.0 | 2.0 | 9.0 | | | |
| | 2.000 | | | 9.0 | 9.0 | | 7.0 | 9.0 | | | | 4.0 | 0.0 | 8.0 | | | |
| | 1.000 | | | 9.0 | 7.0 | | 5.0 | 9.0 | | | | 1.0 | 0.0 | 9.0 | | | |
| | .500 | | | 8.0 | 6.0 | | 2.0 | 9.0 | | | | 0.0 | 0.0 | 1.0 | | | |
| | .250 | | | 5.0 | 0.0 | | 0.0 | 9.0 | | | | 0.0 | 0.0 | 0.0 | | | |
| | .125 | | | 4.0 | 0.0 | | 0.0 | 2.0 | | | | 0.0 | 0.0 | 0.0 | | | |
| 12 | 10.000 | 1.0 | 9.0 | 9.0 | 9.0 | | 0.0 | 7.0 | 9.0 | 0.0 | 0.0 | 0.0 | 0.0 | 0.0 | | | 0.0 |
| | 4.000 | 0.0 | | 9.0 | 2.0 | | 0.0 | | | | | 0.0 | 0.0 | 0.0 | | | |
| | 1.000 | | | 8.0 | | | | | | | | | | | | | |
| 14 | 8.000 | 7.0 | 9.0 | 8.0 | 8.0 | | 0.0 | 9.0 | 9.0 | 0.0 | 0.0 | 0.0 | 0.0 | 3.0 | | | 0.0 |
| | 4.000 | | 9.0 | 8.5 | 1.5 | | 1.5 | 9.0 | | 0.0 | 0.0 | 0.0 | 0.0 | 0.0 | | | 0.0 |
| | 2.000 | | | 0.0 | 0.0 | | 0.0 | 0.0 | | | | | | | | | |
| 16 | 8.000 | 0.0 | 9.0 | 9.0 | 6.0 | | 9.0 | 9.0 | 9.0 | | | | | | 0.0 | | 0.0 |
| | 4.000 | 0.0 | | 9.0 | 0.0 | | 9.0 | 9.0 | 0.0 | | | | | | | | |
| | 1.000 | | | 9.0 | 0.0 | | 0.0 | 0.0 | 0.0 | | | | | | | | |
| 18 | 8.000 | | | 9.0 | 2.0 | 9.0 | 9.0 | 9.0 | | 9.0 | 9.0 | 2.0 | 7.0 | 5.0 | | | |
| | 4.000 | | | 9.0 | 0.0 | 9.0 | 9.0 | 9.0 | | 0.0 | 0.0 | 0.0 | 1.0 | 4.0 | | | |
| | 2.000 | | | 9.0 | 0.0 | | 9.0 | 1.0 | | 0.0 | 0.0 | 0.0 | 1.0 | 4.0 | | | |
| | 1.000 | | | 2.0 | 0.0 | | 1.0 | 0.0 | | 0.0 | 0.0 | 0.0 | 0.0 | 1.0 | | | |
| 19 | 8.000 | | 9.0 | 9.0 | 9.0 | | 9.0 | 9.0 | | 9.0 | 9.0 | 9.0 | 9.0 | 9.0 | | | |
| | 4.000 | | | 9.0 | 9.0 | | 9.0 | 9.0 | | | | 9.0 | 7.0 | 9.0 | | | |
| | 2.000 | | | 9.0 | 9.0 | | 9.0 | 9.0 | | | | 5.0 | 4.0 | 5.5 | | | |
| | 1.000 | | | 9.0 | 9.0 | | 5.0 | 9.0 | | | | 0.0 | 2.5 | 5.0 | | | |
| | .500 | | | 7.0 | 7.0 | | 3.0 | 7.0 | | | | 0.5 | 0.5 | 1.0 | | | |
| | .250 | | | 7.0 | 3.5 | | | | | | | | | | | | |
| 20 | 8.000 | | 9.0 | 9.0 | 3.0 | | 0.0 | 9.0 | | 9.0 | 9.0 | 0.0 | 0.0 | 0.0 | | | |
| | 4.000 | | | 8.0 | 0.0 | | 0.0 | 9.0 | | | | 0.0 | 0.0 | 0.0 | | | |
| | 2.000 | | | 1.0 | 0.0 | | 0.0 | 0.0 | | | | 0.0 | 0.0 | 0.0 | | | |
| 21 | 8.000 | | 9.0 | 9.0 | 8.0 | | 9.0 | 9.0 | | 0.0 | 9.0 | 2.0 | 0.0 | 0.0 | | | |
| | 4.000 | | | 9.0 | 3.0 | | 2.0 | 9.0 | | | | 2.0 | 0.0 | 0.0 | | | |
| | 2.000 | | | 9.0 | 1.0 | | 0.0 | 8.0 | | | | 0.0 | 0.0 | 0.0 | | | |
| 22 | 8.000 | | 9.0 | 9.0 | 9.0 | | 7.0 | 9.0 | | 9.0 | 9.0 | 0.0 | 3.0 | 3.0 | | | |
| | 4.000 | | | 9.0 | 9.0 | | 2.0 | 9.0 | | | | 0.0 | | | | | |
| | 2.000 | | | 7.0 | 3.0 | | 2.0 | 5.0 | | | | 0.0 | | | | | |
| | 1.000 | | | 5.0 | 0.0 | | 0.0 | 0.0 | | | | 0.0 | | | | | |
| 23 | 8.000 | | 9.0 | 9.0 | 9.0 | | 9.0 | 9.0 | | 9.0 | 9.0 | 5.0 | 1.0 | 0.0 | | | |
| | 4.000 | | | 9.0 | 9.0 | | 9.0 | 9.0 | | | | 4.0 | 0.0 | 0.0 | | | |
| | 2.000 | | | 9.0 | 8.0 | | 7.0 | 9.0 | | | | 1.0 | | | | | |
| | 1.000 | | | 9.0 | 5.0 | | 1.0 | 9.0 | | | | 0.0 | | | | | |
| | .500 | | | 9.0 | | | 9.0 | | | | | | | 0.0 | | | |
| 24 | 8.000 | | 9.0 | 9.0 | 8.0 | | 9.0 | 9.0 | | 9.0 | 9.0 | 5.0 | 9.0 | | | | |

TABLE VII-continued
PRE-EMERGENCE TESTS - RATES IN KG/HA

| Compound of Example No. | RATE | BLACK GRASS | LARGE CRAB | GREEN FOX | WILD OATS | LAMBS QTRS | MRNGL RY SP | WILD MUSTD | RED PIGWED | RAG-WEED | VELVET-LEAF | CORN FIELD | COTTON | SOYBEAN AD | SUNFLR XXX | BAR-LEY | S WHEAT ER |
|---|---|---|---|---|---|---|---|---|---|---|---|---|---|---|---|---|---|
| | 4.000 | | | 9.0 | 9.0 | | 9.0 | 9.0 | | | | 0.0 | 1.0 | 9.0 | | | |
| | 2.000 | | | 9.0 | 8.0 | | 3.0 | 9.0 | | | | 0.0 | 1.0 | 8.0 | | | |
| | 1.000 | | | 9.0 | 7.0 | | 2.0 | 9.0 | | | | 0.0 | 0.0 | 1.0 | | | |
| | .500 | | | 5.0 | 5.0 | | 0.0 | 9.0 | | | | 0.0 | 0.0 | 0.0 | | | |
| 27 | 8.000 | | 9.0 | 9.0 | 9.0 | | 9.0 | 9.0 | | 9.0 | 9.0 | 3.0 | 9.0 | 9.0 | | | |
| | 4.000 | | | 9.0 | 9.0 | | 9.0 | 9.0 | | | | 1.0 | 1.0 | 9.0 | | | |
| | 2.000 | | | 9.0 | 7.0 | | 5.0 | 9.0 | | | | 0.0 | 0.0 | 5.0 | | | |
| | 1.000 | | | 9.0 | 5.0 | | 1.0 | 9.0 | | | | 0.0 | 0.0 | 3.0 | | | |
| | .500 | | | 8.0 | 3.0 | | 0.0 | 9.0 | | | | 0.0 | 0.0 | 1.0 | | | |
| | .250 | | | 5.0 | 1.0 | | 0.0 | 9.0 | | | | 0.0 | 0.0 | 0.0 | | | |
| | .125 | | | | | | | | | | | | | | | | |
| 28 | 8.000 | | 9.0 | 9.0 | 9.0 | | 8.0 | 9.0 | | 9.0 | 9.0 | 5.0 | 9.0 | 9.0 | | | |
| | 4.000 | | | 9.0 | 9.0 | | 7.0 | 9.0 | | | | 3.0 | 3.0 | 8.0 | | | |
| | 2.000 | | | 9.0 | 7.0 | | 5.0 | 9.0 | | | | 1.0 | 1.0 | 1.0 | | | |
| | 1.000 | | | 9.0 | 5.0 | | 3.0 | 9.0 | | | | 0.0 | 0.0 | 0.0 | | | |
| | .500 | | | 9.0 | 2.0 | | 1.0 | 7.0 | | | | 0.0 | 0.0 | 0.0 | | | |
| | .250 | | | 7.0 | 0.0 | | 0.0 | 2.0 | | | | | | | | | |
| 29 | 8.000 | | 9.0 | 9.0 | 9.0 | | 9.0 | 9.0 | | 9.0 | 9.0 | 8.0 | 9.0 | 9.0 | | | |
| | 4.000 | | | 9.0 | 9.0 | | 9.0 | 9.0 | | | | 5.0 | 9.0 | 8.0 | | | |
| | 2.000 | | | 9.0 | 9.0 | | 9.0 | 9.0 | | | | 4.0 | 8.0 | 7.0 | | | |
| | 1.000 | | | 9.0 | 9.0 | | 5.0 | 9.0 | | | | 2.0 | 2.0 | 1.0 | | | |
| | .500 | | | 9.0 | 5.0 | | 3.0 | 9.0 | | | | 0.0 | 1.0 | 0.0 | | | |
| | .250 | | | 9.0 | 1.0 | | 1.0 | 9.0 | | | | 0.0 | 0.0 | 0.0 | | | |
| | .125 | | | | | | | | | | | | | | | | |

TABLE VII

PRE-EMERGENCE TESTS - RATES IN KG/HA

| Compound of Example No. | RATE | BLACK GRASS | LARGE CRAB | GREEN FOX | WILD OATS | LAMBS QTRS | MRNGL RY SP | WILD MUSTD | RED PIGWED | RAG-WEED | VELVET-LEAF | CORN FIELD | COTTON | SOYBEAN AD | SUNFLR XXX | BAR-LEY | S WHEAT ER |
|---|---|---|---|---|---|---|---|---|---|---|---|---|---|---|---|---|---|
| 1 | 5.000 | | 9.0 | 9.0 | 9.0 | 9.0 | 9.0 | 9.0 | 9.0 | 9.0 | 9.0 | 8.6 | 8.8 | 9.0 | | | 5.5 |
|   | 4.000 | 9.0 | | 9.0 | 9.0 | 9.0 | 9.0 | 9.0. | 9.0 | 9.0 | 9.0 | 7.2 | 8.1 | 9.0 | 2.0 | 8.0 | 9.0 |
|   | 2.000 | | | 9.0 | 9.0 | 9.0 | 8.3 | 9.0 | 9.0 | 9.0 | | 3.2 | 5.2 | 8.5 | | | 5.0 |
|   | 1.000 | 9.0 | | 9.0 | 9.0 | 9.0 | 6.7 | 9.0 | 9.0 | 9.0 | | 1.5 | 1.9 | 6.1 | | | 4.5 |
|   | .500 | 9.0 | | 8.9 | 7.1 | | 4.6 | 9.0 | 9.0 | 5.0 | | 0.4 | 1.0 | 4.3 | 0.0 | 3.0 | 1.0 |
|   | .250 | 9.0 | | 4.8 | 4.4 | | 1.8 | 8.6 | 9.0 | | | 0.3 | 0.4 | 2.4 | 0.0 | 0.0 | 0.0 |
|   | .125 | | | | 0.6 | | 0.2 | 0.0 | | | | | | | | | |
| 2 | 4.000 | 9.0 | | 9.0 | 9.0 | 9.0 | 8.5 | 9.0 | 9.0 | 9.0 | 9.0 | 1.0 | 2.0 | 5.0 | 0.0 | | 9.0 |
|   | 2.000 | 9.0 | | 9.0 | 6.0 | 9.0 | 4.5 | 9.0 | 9.0 | 7.0 | 9.0 | 1.0 | 0.5 | 2.0 | 0.0 | | 9.0 |
|   | 1.000 | 7.0 | | 9.0 | 2.0 | 9.0 | 0.5 | 9.0 | 8.0 | 2.0 | 9.0 | 1.0 | 0.0 | 1.0 | 0.0 | | 7.0 |
|   | .500 | 4.0 | | 8.0 | 0.0 | 9.0 | 0.5 | 9.0 | 8.0 | 1.0 | 2.0 | 0.0 | 0.0 | 1.0 | | | 6.0 |
|   | .250 | 2.0 | 9.0 | 2.5 | 0.0 | 2.0 | 0.0 | 0.0 | 1.0 | 3.0 | 9.0 | 0.0 | 0.0 | 1.0 | | | 2.0 |
| 3 | 8.000 | | | | | | 0.0 | 9.0 | 9.0 | 7.0 | 9.0 | 0.0 | 0.0 | | | | 0.0 |
|   | 4.000 | 9.0 | | 9.0 | 9.0 | 9.0 | 7.0 | 9.0 | 9.0 | 0.0 | 9.0 | 0.0 | 0.0 | | 0.0 | 0.0 | 0.0 |
|   | 1.000 | 6.0 | | 9.0 | 5.0 | 9.0 | 0.0 | 9.0 | 9.0 | 0.0 | 9.0 | 0.0 | 0.0 | | 0.0 | 0.0 | 0.0 |
|   | .500 | 0.0 | | 9.0 | 0.0 | 9.0 | 0.0 | 9.0 | 9.0 | 0.0 | 2.0 | 0.0 | 0.0 | | 0.0 | 0.0 | 0.0 |
|   | .250 | 0.0 | 9.0 | 0.0 | 0.0 | 2.0 | 0.0 | 0.0 | 8.0 | 0.0 | 9.0 | 0.0 | 0.0 | | | | |
| 4 | 8.000 | | | 9.0 | 9.0 | 9.0 | 9.0 | 9.0 | 9.0 | 3.0 | 9.0 | 0.0 | 0.0 | | | | |
|   | 4.000 | 9.0 | | 9.0 | 9.0 | 9.0 | 9.0 | 9.0 | 9.0 | 7.0 | 9.0 | 0.0 | 0.0 | | | | |
|   | 1.000 | 9.0 | | 9.0 | 5.0 | 9.0 | 9.0 | 9.0 | 9.0 | 0.0 | 9.0 | 0.0 | 0.0 | | | | |
|   | .500 | 5.0 | | 7.0 | 0.0 | | 9.0 | 0.0 | 8.0 | 0.0 | 9.0 | 0.0 | 3.0 | | | | |
|   | .250 | 0.0 | | 0.0 | 0.0 | | 5.0 | 0.0 | 0.0 | 0.0 | 0.0 | 0.0 | 0.0 | | | | |
| 5 | 8.000 | | 9.0 | 9.0 | 9.0 | 9.0 | 9.0 | 9.0 | | 9.0 | 9.0 | 0.0 | 0.0 | 7.0 | 5.0 | 8.0 | 8.0 |
|   | 5.000 | | 9.0 | 9.0 | 8.5 | 9.0 | 9.0 | 9.0 | | 9.0 | 9.0 | | | 1.0 | 0.0 | 7.0 | 8.0 |
|   | 4.000 | | 9.0 | 9.0 | 7.0 | | 9.0 | 9.0 | | 9.0 | 9.0 | 2.7 | 5.5 | 0.7 | 3.7 | 3.0 | 6.0 |
|   | 2.000 | 9.0 | | 9.0 | 4.5 | | 9.0 | 9.0 | | 0.0 | 9.0 | | 0.0 | 0.0 | | 0.0 | 5.0 |
|   | 1.000 | 8.0 | 8.0 | 5.0 | 2.0 | | 0.5 | 7.0 | 8.0 | 2.0 | 9.0 | 0.0 | 2.3 | | 0.3 | | 6.0 |
|   | .500 | | | | 0.0 | | | 1.0 | | | | | 0.0 | | | | 7.0 |
| 6 | 8.000 | | 9.0 | 9.0 | 9.0 | | 9.0 | 9.0 | | 9.0 | 9.0 | 2.0 | 2.0 | 9.0 | | | 0.8 |
|   | 4.000 | | | 9.0 | 8.0 | | 5.0 | 9.0 | | 9.0 | | 1.0 | 1.0 | 9.0 | | | 0.0 |
|   | 2.000 | | | 9.0 | 1.0 | | 1.0 | 9.0 | | | | 0.0 | 1.0 | 8.0 | | | |
|   | 1.000 | | | 7.0 | 0.0 | | 0.0 | 5.0 | | | | 0.0 | 0.0 | 5.0 | | | |
|   | .500 | | | 5.0 | 0.0 | | 0.0 | 2.0 | | | | | | | | | |
| 7 | 8.000 | | | 9.0 | 6.0 | | 2.0 | 9.0 | | 0.0 | 9.0 | 1.7 | 0.7 | 4.0 | 2.0 | | |
|   | 4.000 | 9.0 | 9.0 | 9.0 | 4.5 | | 5.5 | 9.0 | 9.0 | 6.0 | 9.0 | 2.0 | 1.0 | 3.0 | | | |
|   | 2.000 | | | 9.0 | 1.0 | | 1.0 | 9.0 | | | | 0.0 | 0.0 | 0.7 | 0.0 | | 2.0 |
|   | 1.000 | | | 9.0 | 0.0 | | 0.0 | 7.0 | | 2.0 | | 0.0 | 0.0 | 2.0 | | | |
|   | .500 | | | 7.0 | 0.0 | | 0.0 | 1.0 | | | | 5.0 | 3.0 | 9.0 | | | |
| 8 | 4.000 | | | 9.0 | 8.0 | | 9.0 | 9.0 | | | | 4.0 | 2.0 | 7.0 | | | |
|   | 2.000 | | | 9.0 | 7.0 | | 5.0 | 9.0 | | | | 1.0 | 2.0 | 5.0 | | | |
|   | 1.000 | | | 7.0 | 1.0 | | 1.0 | 9.0 | | | | 0.0 | 0.0 | 4.0 | | | |
|   | .50 | | | 1.0 | 0.0 | | 0.0 | 2.0 | | | | | | | | | |
| 9 | 8.000 | | 9.0 | 9.0 | 0.0 | | 2.0 | 9.0 | | 9.0 | 9.0 | 3.0 | 8.0 | 9.0 | | | |
|   | 4.000 | 9.0 | | 9.0 | 6.0 | | 8.0 | 9.0 | | | | 3.0 | 9.0 | 9.0 | | | |
|   | 2.000 | | | 9.0 | 4.0 | | 7.0 | 9.0 | | | | 2.0 | 6.0 | 8.0 | | | |
|   | 1.000 | | | 9.0 | 1.0 | | 7.0 | 9.0 | | | | 2.0 | 2.0 | 7.0 | | | |
|   | .500 | | | 8.0 | 7.0 | | 5.0 | 9.0 | | | | 0.0 | 2.0 | 5.0 | | | |
|   | .250 | | | 7.0 | 7.0 | | 1.0 | 9.0 | | | | 0.0 | 0.0 | 4.0 | | | |
|   | .125 | | | | 5.0 | | | | | | | | | | | | |
| 10 | 8.000 | | 9.0 | 9.0 | 9.0 | | 9.0 | 9.0 | | 0.0 | 9.0 | | | | | | |

TABLE VII-continued

PRE-EMERGENCE TESTS - RATES IN KG/HA

| Compound of Example No. | RATE | BLACK GRASS | LARGE CRAB | GREEN FOX | WILD OATS | LAMBS QTRS | MRNGL RY SP | WILD MUSTD | RED PIGWED | RAG-WEED | VELVET-LEAF | CORN FIELD | COTTON | SOYBEAN AD | SUNFLR XXX | BAR-LEY | S WHEAT ER |
|---|---|---|---|---|---|---|---|---|---|---|---|---|---|---|---|---|---|
|  | 4.000 |  |  | 9.0 | 7.0 |  | 0.0 | 9.0 |  |  |  | 0.0 | 5.0 | 8.0 |  |  |  |
|  | 2.000 |  |  | 9.0 | 5.0 |  | 0.0 | 9.0 |  |  |  | 0.0 | 2.0 | 7.0 |  |  |  |
|  | 1.000 |  |  | 9.0 | 5.0 |  | 0.0 | 8.0 |  |  |  | 0.0 | 1.0 | 5.0 |  |  |  |
|  | .500 |  |  | 7.0 | 1.0 |  | 0.0 | 5.0 |  |  |  | 0.0 | 0.0 | 2.0 |  |  |  |
|  | .250 |  |  | 1.0 | 0.0 |  | 0.0 | 0.0 |  |  |  | 0.0 | 0.0 | 0.0 |  |  |  |
| 11 | 4.000 |  |  | 9.0 | 9.0 |  | 0.0 | 9.0 |  |  |  | 7.0 | 2.0 | 9.0 |  |  |  |
|  | 2.000 |  |  | 9.0 | 9.0 |  | 9.0 | 9.0 |  |  |  | 4.0 | 0.0 | 8.0 |  |  |  |
|  | 1.000 |  |  | 9.0 | 7.0 |  | 7.0 | 9.0 |  |  |  | 1.0 | 0.0 | 9.0 |  |  |  |
|  | .500 |  |  | 8.0 | 6.0 |  | 5.0 | 9.0 |  |  |  | 0.0 | 0.0 | 1.0 |  |  |  |
|  | .250 |  |  | 5.0 | 0.0 |  | 2.0 | 9.0 |  |  |  | 0.0 | 0.0 | 0.0 |  |  |  |
|  | .125 |  |  | 4.0 | 0.0 |  | 0.0 | 2.0 |  |  |  | 0.0 | 0.0 | 0.0 |  |  |  |
| 12 | 10.000 |  |  | 9.0 | 2.0 |  | 0.0 | 7.0 | 9.0 | 0.0 | 0.0 |  |  |  |  |  | 0.0 |
| 14 | 4.000 | 1.0 | 9.0 | 9.0 | 8.0 |  | 0.0 | 9.0 |  |  |  |  |  | 0.0 |  |  |  |
|  | 1.000 | 0.0 |  | 8.0 | 1.5 |  | 1.5 | 9.0 |  | 0.0 | 9.0 |  |  | 0.0 |  |  |  |
|  | 8.000 | 7.0 | 9.0 | 9.0 | 0.0 |  | 0.0 | 9.0 | 9.0 | 0.0 | 0.0 |  | 0.0 | 3.0 | 0.0 | 0.0 | 0.0 |
|  | 4.000 |  | 9.0 | 8.5 | 6.0 |  | 9.0 | 9.0 |  |  |  |  | 0.0 | 0.0 |  |  | 0.0 |
| 16 | 8.000 |  | 9.0 | 9.0 | 0.0 | 9.0 | 0.0 | 9.0 | 9.0 |  | 9.0 |  |  |  |  |  |  |
|  | 4.000 | 0.0 |  | 9.0 | 9.0 | 9.0 | 9.0 | 0.0 | 0.0 |  | 0.0 |  |  |  |  |  |  |
|  | 1.000 | 0.0 |  | 9.0 | 9.0 |  | 9.0 | 9.0 | 0.0 | 9.0 | 0.0 |  |  |  |  |  |  |
| 18 | 8.000 |  | 9.0 | 9.0 | 2.0 |  | 9.0 | 9.0 |  |  |  | 2.0 | 7.0 | 5.0 |  |  |  |
|  | 4.000 |  |  | 9.0 | 1.0 |  | 9.0 | 1.0 |  |  |  | 0.0 | 1.0 | 4.0 |  |  |  |
|  | 2.000 |  |  | 9.0 | 0.0 |  | 9.0 | 0.0 |  |  |  | 0.0 | 1.0 | 4.0 |  |  |  |
|  | 1.000 |  |  | 2.0 | 0.0 |  | 1.0 | 0.0 |  |  |  | 0.0 | 0.0 | 1.0 |  |  |  |
| 19 | 8.000 |  | 9.0 | 9.0 | 9.0 |  | 9.0 | 9.0 |  | 9.0 | 9.0 | 9.0 | 9.0 | 9.0 |  |  |  |
|  | 4.000 |  |  | 9.0 | 9.0 |  | 9.0 | 9.0 |  |  |  | 9.0 | 7.0 | 9.0 |  |  |  |
|  | 2.000 |  |  | 9.0 | 9.0 |  | 9.0 | 9.0 |  |  |  | 5.0 | 4.0 | 5.5 |  |  |  |
|  | 1.000 |  |  | 9.0 | 9.0 |  | 5.0 | 9.0 |  |  |  | 0.0 | 2.5 | 5.0 |  |  |  |
|  | .500 |  |  | 7.0 | 7.0 |  | 3.0 | 7.0 |  |  |  | 0.5 | 0.5 | 1.0 |  |  |  |
|  | .250 |  |  |  | 3.5 |  |  |  |  |  |  |  |  |  |  |  |  |
| 20 | 8.000 |  | 9.0 | 9.0 | 3.0 |  | 9.0 | 9.0 |  | 9.0 | 9.0 | 0.0 | 0.0 | 0.0 |  |  |  |
|  | 4.000 |  |  | 9.0 | 0.0 |  | 0.0 | 9.0 |  |  |  | 0.0 | 0.0 | 0.0 |  |  |  |
|  | 2.000 |  |  | 8.0 | 0.0 |  | 0.0 | 9.0 |  |  |  | 0.0 | 0.0 | 0.0 |  |  |  |
|  | 1.000 |  |  | 1.0 | 0.0 |  | 0.0 | 0.0 |  |  |  | 0.0 | 0.0 | 0.0 |  |  |  |
| 21 | 8.000 |  | 9.0 | 9.0 | 8.0 |  | 9.0 | 9.0 |  | 0.0 | 9.0 | 2.0 | 0.0 | 0.0 |  |  |  |
|  | 4.000 |  |  | 9.0 | 3.0 |  | 2.0 | 9.0 |  |  |  | 2.0 | 0.0 | 0.0 |  |  |  |
|  | 1.000 |  |  | 7.0 | 1.0 |  | 0.0 | 8.0 |  |  |  | 0.0 | 0.0 | 0.0 |  |  |  |
| 22 | 8.000 |  | 9.0 | 9.0 | 9.0 |  | 7.0 | 9.0 |  | 9.0 | 9.0 | 0.0 | 3.0 | 3.0 |  |  |  |
|  | 4.000 |  |  | 9.0 | 9.0 |  | 5.0 | 9.0 |  |  |  | 0.0 | 0.0 |  |  |  |  |
|  | 2.000 |  |  | 9.0 | 3.0 |  | 2.0 | 9.0 |  |  |  | 0.0 | 1.0 | 0.0 |  |  |  |
|  | 1.000 |  |  | 7.0 | 3.0 |  | 2.0 | 5.0 |  |  |  | 0.0 | 0.0 | 0.0 |  |  |  |
|  | .500 |  |  | 5.0 | 0.0 |  | 0.0 | 0.0 |  |  |  | 0.0 | 0.0 |  |  |  |  |
| 23 | 8.000 |  | 9.0 | 9.0 | 9.0 |  | 9.0 | 9.0 |  | 9.0 | 9.0 | 5.0 | 9.0 | 0.0 |  |  |  |
|  | 4.000 |  |  | 9.0 | 9.0 |  | 9.0 | 9.0 |  |  |  | 4.0 | 9.0 | 0.0 |  |  |  |
|  | 2.000 |  |  | 9.0 | 8.0 |  | 7.0 | 9.0 |  |  |  | 1.0 | 3.0 |  |  |  |  |
|  | 1.000 |  |  | 9.0 | 5.0 |  | 1.0 | 9.0 |  |  |  | 0.0 | 0.0 | 0.0 |  |  |  |
| 24 | 8.000 |  | 9.0 | 9.0 | 8.0 |  | 9.0 | 9.0 |  | 9.0 | 9.0 |  |  |  |  |  |  |

TABLE VII-continued

PRE-EMERGENCE TESTS - RATES IN KG/HA

| Compound of Example No. | RATE | BLACK GRASS | LARGE CRAB | GREEN FOX | WILD OATS | LAMBS QTRS | MRNGL RY SP | WILD MUSTD | RED PIGWED | RAG-WEED | VELVET-LEAF | CORN FIELD | COTTON | SOYBEAN AD | SUNFLR XXX | BAR-LEY | S WHEAT ER |
|---|---|---|---|---|---|---|---|---|---|---|---|---|---|---|---|---|---|
|  | 4.000 |  |  | 9.0 | 9.0 |  | 9.0 | 9.0 |  |  |  | 0.0 | 1.0 | 9.0 |  |  |  |
|  | 2.000 |  |  | 9.0 | 8.0 |  | 3.0 | 9.0 |  |  |  | 0.0 | 1.0 | 8.0 |  |  |  |
|  | 1.000 |  |  | 9.0 | 7.0 |  | 2.0 | 9.0 |  |  |  | 0.0 | 0.0 | 1.0 |  |  |  |
|  | .500 |  |  | 5.0 | 5.0 |  | 0.0 | 9.0 |  |  |  | 0.0 | 0.0 | 0.0 |  |  |  |
| 27 | 8.000 |  | 9.0 | 9.0 | 9.0 |  | 9.0 | 9.0 |  | 9.0 | 9.0 | 3.0 | 9.0 | 9.0 |  |  |  |
|  | 4.000 |  |  | 9.0 | 9.0 |  | 9.0 | 9.0 |  |  |  | 1.0 | 1.0 | 9.0 |  |  |  |
|  | 2.000 |  |  | 9.0 | 7.0 |  | 5.0 | 9.0 |  |  |  | 0.0 | 0.0 | 5.0 |  |  |  |
|  | 1.000 |  |  | 9.0 | 5.0 |  | 1.0 | 9.0 |  |  |  | 0.0 | 0.0 | 3.0 |  |  |  |
|  | .500 |  |  | 9.0 | 5.0 |  | 0.0 | 9.0 |  |  |  | 0.0 | 0.0 | 1.0 |  |  |  |
|  | .250 |  |  | 8.0 | 3.0 |  | 0.0 | 9.0 |  |  |  | 0.0 | 0.0 | 0.0 |  |  |  |
|  | .125 |  |  | 5.0 | 1.0 |  | 0.0 | 9.0 |  |  |  | 0.0 | 0.0 | 0.0 |  |  |  |
| 28 | 8.000 |  | 9.0 | 9.0 | 9.0 |  | 8.0 | 9.0 |  | 9.0 | 9.0 | 5.0 | 9.0 | 8.0 |  |  |  |
|  | 4.000 |  |  | 9.0 | 9.0 |  | 7.0 | 9.0 |  |  |  | 3.0 | 3.0 |  |  |  |  |
|  | 2.000 |  |  | 9.0 | 7.0 |  | 5.0 | 9.0 |  |  |  | 1.0 | 1.0 | 8.0 |  |  |  |
|  | 1.000 |  |  | 9.0 | 5.0 |  | 3.0 | 9.0 |  |  |  | 0.0 | 0.0 | 1.0 |  |  |  |
|  | .500 |  |  | 9.0 | 2.0 |  | 1.0 | 7.0 |  |  |  | 0.0 | 0.0 | 0.0 |  |  |  |
|  | .250 |  |  | 7.0 | 0.0 |  | 0.0 | 2.0 |  |  |  | 0.0 | 0.0 | 0.0 |  |  |  |
| 29 | 8.000 |  | 9.0 | 9.0 | 9.0 |  | 9.0 | 9.0 |  | 9.0 | 9.0 | 8.0 | 9.0 | 9.0 |  |  |  |
|  | 4.000 |  |  | 9.0 | 9.0 |  | 9.0 | 9.0 |  |  |  | 5.0 | 9.0 | 8.0 |  |  |  |
|  | 2.000 |  |  | 9.0 | 9.0 |  | 9.0 | 9.0 |  |  |  | 4.0 | 8.0 | 7.0 |  |  |  |
|  | 1.000 |  |  | 9.0 | 9.0 |  | 5.0 | 9.0 |  |  |  | 2.0 | 2.0 | 1.0 |  |  |  |
|  | .500 |  |  | 9.0 | 5.0 |  | 3.0 | 9.0 |  |  |  | 0.0 | 1.0 | 0.0 |  |  |  |
|  | .250 |  |  | 9.0 | 1.0 |  | 1.0 | 9.0 |  |  |  | 0.0 | 0.0 | 0.0 |  |  |  |
|  | .125 |  |  |  |  |  |  | 9.0 |  |  |  |  |  |  |  |  |  |

EXAMPLE 68

Preemergence herbicidal evaluation of test compound

The test method described in Example 67 for the preemergence herbicidal evaluation is repeated, excepting that the following plant species are used for the evaluation. Data obtained are reported in Table VIII below.

| Common Name | Scientific Name |
|---|---|
| Barnyardgrass | *Echinochloa crus-galli* |
| Canarygrass | *Phalaris* spp. |
| Crabgrass | *Digitaria sanguinalis* |
| Green Foxtail | *Setaria viridis* |
| Wild Oat | *Avena fatua* |
| Matricaria | *Matricaria* spp. |
| Wild Mustard | *Brassica kaber* |
| Prickly Sida | *Sida spinosa* |
| Smartweed | *Polygonum pennsylvania* |
| Field Corn | *Zea mays* |
| Cotton | *Gossypium hirsutum* |
| Wheat | *Triticum alstivum* |

TABLE VIII

PRE-EMERGENCE TESTS - RATES IN KG/HA

| Compound of Example No. | RATE | BARNYARDGR | CANARYGRAS | CRABGRASS | GREEN FOX | WILD OATS | MATRI CARIA | WILD MUSTD | PRIKY SIDA | PENN SMART | CORN FIELD | COTTON | W WHEAT NU |
|---|---|---|---|---|---|---|---|---|---|---|---|---|---|
| 37d | 4.000 | 8.0 | 9.0 | 9.0 | 9.0 | 0.0 | 9.0 | 9.0 | 9.0 | 2.0 | 0.0 | 0.0 | 0.0 |
|  | 2.000 | 7.0 | 8.0 | 8.0 | 9.0 | 0.0 | 9.0 | 9.0 | 9.0 | 1.0 | 0.0 | 0.0 | 0.0 |
|  | 1.000 | 1.0 | 8.0 | 7.0 | 7.0 | 0.0 | 9.0 | 9.0 | 7.0 | 0.0 | 0.0 | 0.0 | 0.0 |
|  | .500 | 0.0 | 7.0 | 5.0 | 6.0 | 0.0 | 9.0 | 5.0 | 5.0 | 0.0 | 0.0 | 0.0 | 0.0 |
|  | .250 | 0.0 | 2.0 | 0.0 | 2.0 | 0.0 | 9.0 | 0.0 | 0.0 | 0.0 | 0.0 | 0.0 | 0.0 |
|  | .125 | 0.0 | 0.0 | 0.0 | 0.0 | 0.0 | 9.0 | 0.0 | 0.0 | 0.0 | 0.0 | 0.0 | 0.0 |
| 42 | 8.000 | 9.0 | 9.0 | 9.0 | 9.0 | 9.0 | 9.0 | 9.0 | 9.0 | 9.0 | 7.0 | 9.0 | 9.0 |
|  | 4.000 | 9.0 | 9.0 | 9.0 | 9.0 | 9.0 | 9.0 | 9.0 | 9.0 | 9.0 | 4.0 | 9.0 | 9.0 |
|  | 2.000 | 9.0 | 9.0 | 9.0 | 9.0 | 9.0 | 9.0 | 9.0 | 9.0 | 9.0 | 0.0 | 9.0 | 9.0 |
|  | 1.000 | 5.0 | 9.0 | 9.0 | 9.0 | 8.0 | 9.0 | 9.0 | 8.0 | 7.0 | 0.0 | 3.0 | 8.0 |
|  | .500 | 1.0 | 5.0 | 7.0 | 3.0 | 4.0 | 9.0 | 5.0 | 7.0 | 5.0 | 0.0 | 1.0 | 2.0 |
|  | .250 | 0.0 | 0.0 | 5.0 | 0.0 | 0.0 | 8.0 | 0.0 | 0.0 | 0.0 | 0.0 | 0.0 | 0.0 |
| 43 | 8.000 | 9.0 | .0 | 9.0 | 9.0 | 9.0 | 9.0 | 9.0 | 9.0 | 7.0 | 7.5 | 7.0 | 9.0 |
|  | 4.000 | 8.0 | 9.0 | 9.0 | 9.0 | 9.0 | 9.0 | 9.0 | 9.0 | 6.0 | 8.0 | 5.0 | 8.0 |
|  | 2.000 | 7.0 | 9.0 | 9.0 | 7.0 | 9.0 | 9.0 | 9.0 | 9.0 | 5.0 | 1.5 | 1.5 | 7.0 |
|  | 1.000 | 2.5 | 8.0 | 8.0 | 6.5 | 6.5 | 9.0 | 9.0 | 5.0 | 2.0 | 2.0 | 1.0 | 2.0 |
|  | .500 | 0.0 | 5.0 | 2.0 | 5.0 | 1.0 | 9.0 | 3.0 | 0.0 | 0.0 | 0.0 | 0.0 | 0.0 |
|  | .250 | 0.0 | 1.0 | 0.0 | 1.0 | 0.0 | 9.0 | 0.0 | 0.0 | 0.0 | 0.0 | 0.0 | 0.0 |
|  | .125 | 0.0 | 0.0 | 0.0 | 0.0 | 0.0 | 9.0 | 0.0 | 0.0 | 0.0 | 0.0 | 0.0 | 0.0 |
| 44 | 8.000 | 9.0 | 9.0 | 9.0 | 9.0 | 8.0 | 9.0 | 9.0 | 9.0 | 8.0 | 1.8 | 1.0 | 0.0 |
|  | 4.000 | 9.0 | 9.0 | 9.0 | 9.0 | 7.5 | 9.0 | 9.0 | 9.0 | 5.0 | 2.0 | 0.0 | 0.0 |
|  | 2.000 | 9.0 | 9.0 | 9.0 | 9.0 | 1.0 | 9.0 | 9.0 | 8.0 | 1.5 | 0.5 | 0.0 | 0.0 |
|  | 1.000 | 1.0 | 1.0 | 9.0 | 5.0 | 0.5 | 9.0 | 9.0 | 2.0 | 0.0 | 0.0 | 0.0 | 0.0 |
|  | .500 | 0.0 | 0.0 | 5.0 | 1.0 | 0.0 | 9.0 | 1.0 | 0.0 | 0.0 | 0.0 | 0.0 | 0.0 |
|  | .250 | 0.0 | 0.0 | 0.0 | 0.0 | 0.0 | 9.0 | 0.0 | 0.0 | 0.0 | 0.0 | 0.0 | 0.0 |
|  | .125 | 0.0 | 0.0 | 0.0 | 0.0 | 0.0 | 7.0 | 0.0 | 0.0 | 0.0 | 0.0 | 0.0 | 0.0 |
| 45 | 5.000 | 7.0 | 8.0 | 9.0 | 9.0 | 5.0 | 9.0 | 9.0 | 9.0 | 8.0 | 0.0 | 3.0 | 0.0 |
|  | 4.000 | 9.0 | 0.0 | 7.0 | 8.0 | 0.0 | 9.0 | 9.0 | 9.0 | 7.0 | 0.0 | 2.0 | 0.0 |
|  | 2.000 | 0.0 | 0.0 | 4.0 | 5.0 | 0.0 | 9.0 | 9.0 | 2.0 | 5.0 | 0.0 | 1.0 | 0.0 |
|  | 1.000 | 0.0 | 0.0 | 0.0 | 2.0 | 0.0 | 9.0 | 2.0 | 9.0 | 1.0 | 0.0 | 0.0 | 0.0 |
|  | .500 | 0.0 | 0.0 | 0.0 | 0.0 | 0.0 | 9.0 | 0.0 | 9.0 | 7.0 | 0.0 | 0.0 | 0.0 |
| 46 | 4.000 | 9.0 | 9.0 | 9.0 | 9.0 | 9.0 | 9.0 | 9.0 | 9.0 | 1.0 | 0.0 | 3.0 | 9.0 |
|  | 2.000 | 5.0 | 7.0 | 9.0 | 9.0 | 0.0 | 9.0 | 9.0 | 9.0 | 7.0 | 0.0 | 1.0 | 2.0 |
|  | 1.000 | 0.0 | 1.0 | 9.0 | 7.0 | 0.0 | 9.0 | 5.0 | 9.0 | 2.0 | 0.0 | 1.0 | 0.0 |
|  | .500 | 0.0 | 0.0 | 8.0 | 5.0 | 0.0 | 9.0 | 5.0 | 5.0 | 0.0 | 0.0 | 0.0 | 0.0 |
|  | .250 | 0.0 | 0.0 | 5.0 | 2.0 | 0.0 | 7.0 | 0.0 | 1.0 | 0.0 | 0.0 | 0.0 | 0.0 |
|  | .125 | 0.0 | 0.0 | 0.0 | 0.0 | 0.0 | 5.0 | 0.0 | 0.0 | 0.0 | 0.0 | 0.0 | 0.0 |
| 49 | 8.000 | 9.0 | 9.0 | 9.0 | 9.0 | 0.0 | 9.0 | 9.0 | 9.0 | 0.0 | 0.0 | 3.0 | 5.0 |
|  | 4.000 | 2.0 | 8.0 | 7.0 | 9.0 | 3.0 | 9.0 | 9.0 | 9.0 | 0.0 | 0.0 | 2.0 | 1.0 |
|  | 2.000 | 0.0 | 0.0 | 4.0 | 7.0 | 0.0 | 9.0 | 5.0 | 5.0 | 0.0 | 0.0 | 1.0 | 0.0 |
|  | 1.000 | 0.0 | 0.0 | 2.0 | 2.0 | 0.0 | 9.0 | 1.0 | 1.0 | 0.0 | 0.0 | 0.0 | 0.0 |
| 51 | 8.000 | 9.0 | 9.0 | 9.0 | 9.0 | 9.0 | 9.0 | 9.0 | 9.0 | 9.0 | 5.0 | 9.0 | 8.0 |
|  | 4.000 | 9.0 | 9.0 | 9.0 | 9.0 | 7.0 | 9.0 | 9.0 | 9.0 | 9.0 | 2.0 | 1.0 | 5.0 |
|  | 2.000 | 7.0 | 9.0 | 8.0 | 5.0 | 7.0 | 9.0 | 9.0 | 5.0 | 5.0 | 0.0 | 0.0 | 3.0 |
|  | 1.000 | 1.0 | 7.0 | 5.0 | 1.0 | 2.0 | 9.0 | 5.0 | 3.0 | 3.0 | 0.0 | 0.0 | 1.0 |
|  | .500 | 0.0 | 0.0 | 1.0 | 0.0 | 0.0 | 9.0 | 1.0 | 0.0 | 0.0 | 0.0 | 0.0 | 0.0 |
|  | .250 | 0.0 | 0.0 | 0.0 | 0.0 | 0.0 | 9.0 | 0.0 | 0.0 | 0.0 | 0.0 | 0.0 | 0.0 |
|  | .125 | 0.0 | 0.0 | 0.0 | 0.0 | 0.0 | 9.0 | 0.0 | 0.0 | 0.0 | 0.0 | 0.0 | 0.0 |
| 52 | 4.000 | 9.0 | 9.0 | 9.0 | 9.0 | 9.0 | 9.0 | 9.0 | 9.0 | 9.0 | 9.0 | 5.0 | 9.0 |

TABLE VIII-continued

PRE-EMERGENCE TESTS - RATES IN KG/HA

| Compound of Example No. | RATE | BARNYARDGR | CANARYGRAS | CRABGRASS | GREEN FOX | WILD OATS | MATRI CARIA | WILD MUSTD | PRIKY SIDA | PENN SMART | CORN FIELD | COTTON | W WHEAT NU |
|---|---|---|---|---|---|---|---|---|---|---|---|---|---|
| | 2.000 | 9.0 | 9.0 | 9.0 | 9.0 | 9.0 | 9.0 | 9.0 | 9.0 | 9.0 | 9.0 | 4.0 | 9.0 |
| | 1.000 | 9.0 | 9.0 | 9.0 | 9.0 | 9.0 | 9.0 | 9.0 | 9.0 | 9.0 | 6.0 | 2.0 | 9.0 |
| | .500 | 9.0 | 9.0 | 9.0 | 9.0 | 9.0 | 9.0 | 9.0 | 9.0 | 9.0 | 4.0 | 1.0 | 9.0 |
| | .250 | 9.0 | 9.0 | 9.0 | 9.0 | 9.0 | 9.0 | 9.0 | 9.0 | 9.0 | 3.0 | 0.0 | 6.0 |
| | .125 | 5.0 | 9.0 | 9.0 | 9.0 | 5.0 | 9.0 | 9.0 | 9.0 | 7.0 | 3.0 | 0.0 | 2.0 |
| 54 | 8.000 | 9.0 | 8.5 | 9.0 | 9.0 | 9.0 | 9.0 | 9.0 | 9.0 | 7.0 | 0.0 | 3.5 | 1.5 |
| | 4.000 | 8.0 | 8.0 | 9.0 | 9.0 | 6.5 | 7.0 | 9.0 | 8.0 | 5.0 | 0.0 | 0.0 | 1.0 |
| | 2.000 | 4.0 | 5.0 | 8.0 | 6.5 | 1.5 | 4.0 | 5.0 | 5.0 | 3.0 | 0.0 | 0.0 | 0.0 |
| | 1.000 | 0.5 | 0.5 | 3.0 | 1.0 | 0.0 | 2.5 | 4.5 | 0.5 | 0.5 | 0.0 | 0.0 | 0.0 |
| | .500 | 0.0 | 0.0 | 0.0 | 0.0 | 0.0 | 0.5 | 2.5 | 0.0 | 0.0 | 0.0 | 0.0 | 3.0 |
| | .250 | 0.0 | 0.0 | 0.0 | 0.0 | 0.0 | 0.5 | 0.0 | 0.0 | 0.0 | 0.0 | 7.0 | 1.0 |
| 56 | 2.000 | 8.0 | 9.0 | 9.0 | 9.0 | 9.0 | 9.0 | 9.0 | 8.0 | 9.0 | 0.0 | 1.0 | 0.0 |
| | 1.000 | 5.0 | 9.0 | 2.0 | 5.0 | 0.0 | 7.0 | 5.0 | 1.0 | 5.0 | 0.0 | 0.0 | 0.0 |
| | .500 | 0.0 | 7.0 | 0.0 | 0.0 | 0.0 | 7.0 | 0.0 | 0.0 | 0.0 | 0.0 | 0.0 | 0.0 |
| | .250 | 0.0 | 1.0 | 0.0 | 0.0 | 0.0 | 1.0 | 0.0 | 0.0 | 0.0 | 0.0 | 0.0 | 0.0 |
| 57 | 8.000 | 9.0 | 9.0 | 9.0 | 9.0 | 9.0 | 9.0 | 9.0 | 9.0 | 9.0 | 0.0 | 3.0 | 5.0 |
| | 4.000 | 8.0 | 9.0 | 9.0 | 9.0 | 5.0 | 9.0 | 9.0 | 8.0 | 9.0 | 0.0 | 2.0 | 0.0 |
| | 2.000 | 5.0 | 9.0 | 9.0 | 9.0 | 2.0 | 9.0 | 5.0 | 5.0 | 5.0 | 0.0 | 0.0 | 0.0 |
| | 1.000 | 0.0 | 5.0 | 5.0 | 9.0 | 0.0 | 7.0 | 0.0 | 0.0 | 5.0 | 0.0 | 0.0 | 0.0 |
| | .500 | 0.0 | 0.0 | 0.0 | 2.0 | 0.0 | | 0.0 | 3.0 | 0.0 | 0.0 | 0.0 | 0.0 |
| | .250 | 0.0 | 0.0 | 2.0 | 8.0 | 0.0 | | 0.0 | 0.0 | 0.0 | 0.0 | 0.0 | 0.0 |
| 59 | 8.000 | 0.0 | 5.0 | 0.0 | 7.0 | 0.0 | 9.0 | 9.0 | 8.0 | 7.0 | 0.0 | 0.0 | 0.0 |
| | 4.000 | 0.0 | 0.0 | 0.0 | 0.0 | 0.0 | 7.0 | 0.0 | 5.0 | 0.0 | 0.0 | 0.0 | 0.0 |
| | 2.000 | 0.0 | 0.0 | 0.0 | 0.0 | 0.0 | 0.0 | 0.0 | 0.0 | 0.0 | 0.0 | 0.0 | 0.0 |
| 61 | 8.000 | 9.0 | 7.0 | 9.0 | 9.0 | 4.0 | 8.0 | 9.0 | 9.0 | 8.0 | 0.0 | 5.0 | 2.0 |
| | 4.000 | 0.0 | 1.0 | 5.0 | 8.0 | 2.0 | 7.0 | 9.0 | 5.0 | 5.0 | 0.0 | 3.0 | 0.0 |
| | 2.000 | 0.0 | 0.0 | 0.0 | 2.0 | 0.0 | 1.0 | 2.0 | 0.0 | 3.0 | 0.0 | 1.0 | 0.0 |
| | 1.000 | 0.0 | 0.0 | 0.0 | 1.0 | 0.0 | 0.0 | 1.0 | 0.0 | 0.0 | 0.0 | 0.0 | 0.0 |
| | .500 | 0.0 | 0.0 | 0.0 | 0.0 | 0.0 | 0.0 | 0.0 | 0.0 | 0.0 | 0.0 | 0.0 | 0.0 |
| 62 | 8.000 | 6.0 | 9.0 | 9.0 | 9.0 | 9.0 | 9.0 | 9.0 | 9.0 | 9.0 | 7.0 | 9.0 | 9.0 |
| | 4.000 | 9.0 | 9.0 | 9.0 | 9.0 | 8.0 | 9.0 | 9.0 | 9.0 | 9.0 | 3.0 | 5.0 | 9.0 |
| | 2.000 | 1.0 | 9.0 | 5.0 | 3.0 | 5.0 | 9.0 | 9.0 | 8.0 | 9.0 | 1.0 | 2.0 | 3.0 |
| | 1.000 | 0.0 | 5.0 | 1.0 | 2.0 | 1.0 | 7.0 | 2.0 | 9.0 | 5.0 | 0.0 | 1.0 | 1.0 |
| | .500 | 0.0 | 1.0 | 0.0 | 0.0 | 0.0 | 0.0 | 0.0 | 2.0 | 2.0 | 0.0 | 1.0 | 0.0 |
| | .250 | 0.0 | 0.0 | 0.0 | 0.0 | 0.0 | | 0.0 | 0.0 | 0.0 | 0.0 | 0.0 | 0.0 |
| 63 | 4.000 | 9.0 | 9.0 | 9.0 | 9.0 | 9.0 | 9.0 | 9.0 | 9.0 | 9.0 | 8.5 | 5.0 | 9.0 |
| | 2.000 | 9.0 | 9.0 | 9.0 | 9.0 | 9.0 | 9.0 | 9.0 | 9.0 | 9.0 | 8.5 | 2.0 | 9.0 |
| | 1.000 | 8.7 | 9.0 | 9.0 | 9.0 | 8.5 | 9.0 | 9.0 | 9.0 | 8.7 | 8.0 | 1.3 | 8.5 |
| | .500 | 8.3 | 9.0 | 9.0 | 9.0 | 7.0 | 9.0 | 9.0 | 7.0 | 8.7 | 7.0 | 0.7 | 8.5 |
| | .250 | 4.3 | 9.0 | 9.0 | 9.0 | 5.0 | 9.0 | 7.0 | 3.0 | 6.0 | 5.5 | 0.3 | 7.0 |
| | .125 | | 8.5 | | | | | 5.0 | | | 3.5 | 0.0 | 5.5 |
| 65 | 8.000 | 9.0 | 9.0 | 9.0 | 9.0 | 9.0 | 9.0 | 9.0 | 9.0 | 9.0 | 0.0 | 0.0 | 5.0 |
| | 4.000 | 7.0 | 8.0 | 9.0 | 9.0 | 7.0 | 9.0 | 7.0 | 7.0 | 8.0 | 0.0 | 0.0 | 2.0 |
| | 2.000 | 5.0 | 2.0 | 3.0 | 3.0 | 2.0 | 5.0 | 5.0 | 7.0 | 5.0 | 0.0 | 0.0 | 0.0 |
| | 1.000 | 1.0 | | | | | | | | | | | |
| 33 | 10.000 | 9.0 | 7.4 | 8.9 | 9.0 | 9.0 | 1.0 | 7.8 | 8.0 | 0.0 | 3.2 | 2.3 | 8.0 |
| | 4.000 | 8.0 | 6.1 | 8.1 | 7.8 | 6.8 | 0.0 | 7.2 | 4.5 | 0.0 | 2.1 | 1.1 | 4.0 |
| | 2.000 | 5.8 | 4.9 | 7.1 | 7.8 | 5.1 | 0.0 | 3.5 | 0.0 | 0.0 | 0.3 | 1.0 | 0.0 |
| | 1.000 | 4.2 | | | | 4.3 | | | | | | | |

TABLE VIII-continued
PRE-EMERGENCE TESTS - RATES IN KG/HA

| Compound of Example No. | RATE | BARNYARDGR | CANARYGRAS | CRABGRASS | GREEN FOX | WILD OATS | MATRI CARIA | WILD MUSTD | PRIKY SIDA | PENN SMART | CORN FIELD | COTTON | W WHEAT NU |
|---|---|---|---|---|---|---|---|---|---|---|---|---|---|
| | .500 | 1.3 | 1.4 | 3.1 | 6.6 | 1.0 | 0.0 | 0.6 | 0.0 | 0.0 | 0.2 | 0.4 | 0.0 |
| | .250 | 0.0 | 1.0 | 2.5 | 2.4 | 0.2 | 0.0 | 0.0 | 0.0 | 0.0 | 0.0 | 0.0 | 0.0 |
| 35 | 10.000 | 0.0 | | | 5.0 | 0.0 | | 9.0 | 8.0 | | | | |
| | 4.000 | 3.0 | | | 3.0 | | | 9.0 | 9.0 | | | | |
| | 1.000 | 0.0 | | | 0.0 | | | 0.0 | 9.0 | | | | |
| 38 | 4.000 | 8.0 | 9.0 | 9.0 | 9.0 | 7.0 | 9.0 | 9.0 | 9.0 | 9.0 | 0.0 | 3.0 | 8.0 |
| | 2.000 | 8.0 | 9.0 | 9.0 | 9.0 | 7.0 | 9.0 | 9.0 | 9.0 | 9.0 | 0.0 | 1.0 | 4.0 |
| | 1.000 | 3.0 | 9.0 | 5.0 | 9.0 | 5.0 | 9.0 | 9.0 | 9.0 | 3.0 | 0.0 | 0.0 | 1.0 |
| | .500 | 1.0 | 1.0 | 1.0 | 1.0 | 1.0 | 9.0 | 9.0 | 5.0 | 1.0 | 0.0 | 0.0 | 0.0 |
| | .250 | 0.0 | 0.0 | 0.0 | 0.0 | 0.0 | 0.0 | 1.0 | 0.0 | 0.0 | 0.0 | 0.0 | 0.0 |
| | .125 | 0.0 | 0.0 | 0.0 | 0.0 | 0.0 | 5.0 | 0.0 | 0.0 | 0.0 | 0.0 | 0.0 | 0.0 |
| 24c | 5.000 | 8.0 | | | 0.0 | 6.0 | | | 9.0 | | | | |
| | 4.000 | 9.0 | 9.0 | 9.0 | 9.0 | 8.0 | 9.0 | 9.0 | 9.0 | 9.0 | 3.0 | 2.0 | 5.0 |
| | 2.000 | 3.0 | 9.0 | 9.0 | 9.0 | 1.0 | 9.0 | 9.0 | 9.0 | 9.0 | 1.0 | 1.0 | 4.0 |
| | 1.000 | 0.0 | 9.0 | 9.0 | 9.0 | 0.0 | 9.0 | 9.0 | 9.0 | 7.0 | 0.0 | 0.0 | 1.0 |
| | .500 | 0.0 | 8.0 | 1.0 | 7.0 | 0.0 | 5.0 | 1.0 | 7.0 | 3.0 | 0.0 | 0.0 | 0.0 |
| | .250 | 0.0 | 5.0 | 0.0 | 1.0 | 0.0 | 0.0 | 1.0 | 1.0 | 0.0 | 0.0 | 0.0 | 0.0 |
| 50a | 4.000 | 5.0 | 9.0 | 9.0 | 9.0 | 7.0 | 9.0 | 9.0 | 9.0 | 5.0 | 0.0 | 3.0 | 7.0 |
| | 2.000 | 0.0 | 9.0 | 9.0 | 9.0 | 1.0 | 9.0 | 9.0 | 9.0 | 1.0 | 0.0 | 1.0 | 1.0 |
| | 1.000 | 0.0 | 8.0 | 1.0 | 7.0 | 0.0 | 9.0 | 9.0 | 9.0 | 0.0 | 0.0 | 0.0 | 0.0 |
| | .500 | 0.0 | 5.0 | 0.0 | 1.0 | 0.0 | 9.0 | 9.0 | 1.0 | 0.0 | 0.0 | 0.0 | 0.0 |
| | .250 | 0.0 | 1.0 | 0.0 | 0.0 | 0.0 | 9.0 | 9.0 | 0.0 | 0.0 | 0.0 | 0.0 | 0.0 |
| | .125 | 0.0 | 0.0 | 0.0 | 0.0 | 0.0 | 9.0 | 9.0 | 0.0 | 0.0 | 0.0 | 0.0 | 0.0 |
| 37e | 8.000 | 9.0 | 9.0 | 9.0 | 9.0 | 0.0 | 9.0 | 9.0 | 9.0 | 9.0 | 0.0 | 0.0 | 0.0 |
| | 4.000 | 8.0 | 8.0 | 8.0 | 9.0 | 5.0 | 9.0 | 9.0 | 9.0 | 7.0 | 0.0 | 0.0 | 0.0 |
| | 2.000 | 3.0 | 5.0 | 3.0 | 5.0 | 4.0 | 7.0 | 9.0 | 5.0 | 5.0 | 0.0 | 0.0 | 0.0 |
| | 1.000 | 0.0 | 1.0 | 0.0 | 1.0 | 1.0 | 5.0 | 5.0 | 5.0 | 0.0 | 0.0 | 0.0 | 0.0 |
| | .500 | 0.0 | 0.0 | 0.0 | 0.0 | 0.0 | | 1.0 | 0.0 | | | | |
| 24d | 8.000 | 9.0 | 8.0 | 9.0 | 9.0 | 9.0 | 9.0 | 9.0 | 9.0 | 0.0 | 0.0 | 0.0 | 0.0 |
| | 2.000 | 5.0 | 0.0 | 0.0 | 5.0 | 0.0 | 0.0 | 1.0 | 8.0 | 0.0 | 0.0 | 0.0 | 0.0 |
| | 1.000 | 0.0 | | | 1.0 | 0.0 | | 0.0 | 5.0 | | | | |
| 34 | 8.000 | 9.0 | 9.0 | 9.0 | 9.0 | 3.0 | 5.0 | 9.0 | 9.0 | 0.0 | 3.0 | 0.0 | 3.0 |
| | 4.000 | 8.0 | 8.0 | 8.0 | 9.0 | 3.0 | 5.0 | 5.0 | 3.0 | 0.0 | 2.0 | 0.0 | 2.0 |
| | 2.000 | 1.0 | 5.0 | 5.0 | 5.0 | 0.0 | 1.0 | 5.0 | 1.0 | 0.0 | 0.0 | 0.0 | 0.0 |
| | 1.000 | 0.0 | 1.0 | 0.0 | 0.0 | 0.0 | 0.0 | 1.0 | 0.0 | | | | |
| 24e | 8.000 | 9.0 | 8.0 | 9.0 | 9.0 | 6.0 | 9.0 | 9.0 | 9.0 | 9.0 | 0.0 | 0.0 | 9.0 |
| | 2.000 | 7.0 | 0.0 | 0.0 | 8.0 | 7.0 | 9.0 | 5.0 | 8.0 | 9.0 | 0.0 | 0.0 | 8.0 |
| | 1.000 | 0.0 | | | 8.0 | 5.0 | 9.0 | 0.0 | 5.0 | 5.0 | 0.0 | 0.0 | 5.0 |
| 53 | 8.000 | 3.0 | 9.0 | 9.0 | 9.0 | 0.0 | 9.0 | 9.0 | 9.0 | 9.0 | 0.0 | 2.0 | 0.0 |
| | 2.000 | 0.0 | 9.0 | 9.0 | 0.0 | 0.0 | 9.0 | 5.0 | 8.0 | 1.0 | 0.0 | 0.0 | 0.0 |
| | 1.000 | 0.0 | 5.0 | 8.0 | 0.0 | 0.0 | | 0.0 | 2.0 | 0.0 | 0.0 | 0.0 | 0.0 |
| 24f | 8.000 | 0.0 | 9.0 | 5.0 | 9.0 | 0.0 | 9.0 | 3.0 | 9.0 | 3.0 | 0.0 | 0.0 | 3.0 |
| | 2.000 | 0.0 | 0.0 | 0.0 | 0.0 | 0.0 | 9.0 | 0.0 | 5.0 | 0.0 | 0.0 | 0.0 | 0.0 |
| | 1.000 | 0.0 | 0.0 | 0.0 | 0.0 | 0.0 | 9.0 | 0.0 | 0.0 | 0.0 | 0.0 | 0.0 | 0.0 |
| | .500 | 0.0 | 0.0 | 0.0 | 0.0 | 0.0 | 5.0 | 0.0 | 0.0 | 0.0 | 0.0 | 0.0 | 0.0 |
| | .250 | 0.0 | | | 0.0 | 0.0 | | 0.0 | 0.0 | | | | |
| 66 | 8.000 | 9.0 | 0.0 | 0.0 | 9.0 | 4.0 | 9.0 | 9.0 | 9.0 | 9.0 | 0.0 | 0.0 | |
| | 4.000 | 9.0 | 0.0 | 0.0 | 9.0 | 9.0 | 5.0 | 9.0 | 9.0 | | 6.0 | 2.5 | |

TABLE VIII-continued
PRE-EMERGENCE TESTS - RATES IN KG/HA

| Compound of Example No. | RATE | BARNYARDGR | CANARYGRAS | CRABGRASS | GREEN FOX | WILD OATS | MATRI CARIA | WILD MUSTD | PRIKY SIDA | PENN SMART | CORN FIELD | COTTON | W WHEAT NU |
|---|---|---|---|---|---|---|---|---|---|---|---|---|---|
| | 2.000 | 8.0 | 9.0 | 9.0 | 9.0 | 9.0 | 9.0 | 9.0 | 8.0 | 9.0 | 9.0 | 0.0 | 5.0 |
| | 1.000 | 4.5 | 9.0 | 9.0 | 9.0 | 3.5 | 9.0 | 4.5 | 4.5 | 5.5 | 1.7 | 0.0 | 1.0 |
| | .500 | 2.0 | 5.0 | 8.0 | 7.0 | 1.0 | 7.0 | 9.0 | 0.0 | 5.0 | 0.0 | 0.0 | 0.0 |
| | .250 | 0.0 | 2.0 | 1.0 | 0.0 | 0.0 | 5.0 | 5.0 | 0.0 | 0.0 | 0.0 | 0.0 | 0.0 |
| 24h | 8.000 | 9.0 | | | 9.0 | 7.0 | | 9.0 | 9.0 | 9.0 | 2.0 | 6.0 | |
| | 4.000 | 4.0 | | | 8.0 | 0.0 | | 8.0 | 8.0 | 9.0 | 8.0 | 1.0 | 5.0 |
| | 2.000 | 7.0 | 9.0 | 5.0 | 9.0 | 7.0 | 9.0 | 9.0 | 6.0 | 7.0 | 1.0 | 0.0 | 0.0 |
| | 1.000 | 2.5 | 5.0 | 3.0 | 4.0 | 2.5 | 9.0 | 9.0 | 1.0 | 9.0 | 0.0 | 0.0 | 0.0 |
| | .500 | 0.0 | 3.0 | 1.0 | 5.0 | 1.0 | 9.0 | 5.0 | 0.0 | 5.0 | 0.0 | 0.0 | 0.0 |
| | .250 | 0.0 | 2.0 | 0.0 | 3.0 | 0.0 | 9.0 | 5.0 | 0.0 | 5.0 | 0.0 | 0.0 | 0.0 |
| | .125 | 0.0 | 0.0 | 0.0 | 1.0 | 0.0 | 7.0 | 1.0 | 0.0 | 4.0 | 0.0 | 0.0 | 0.0 |
| 24g | 8.000 | 8.0 | | | 9.0 | 0.0 | | 9.0 | 9.0 | 9.0 | 0.5 | 0.0 | 0.0 |
| | 4.000 | 6.0 | | | 9.0 | 1.0 | 9.0 | 9.0 | 8.0 | 8.0 | 0.0 | 0.0 | 0.0 |
| | 2.000 | 5.0 | 3.0 | 0.0 | 8.0 | 0.0 | 9.0 | 0.5 | 0.5 | 4.0 | 0.0 | 0.0 | 0.0 |
| | 1.000 | 2.0 | 0.0 | 0.0 | 5.5 | 0.0 | 9.0 | 0.0 | 0.0 | 1.0 | 0.0 | 0.0 | 0.0 |
| | .500 | 0.0 | 0.0 | 0.0 | 3.0 | 0.0 | 9.0 | 0.0 | 0.0 | 0.0 | 0.0 | 0.0 | 0.0 |
| | .250 | 0.0 | 0.0 | 0.0 | 0.0 | 0.0 | 5.0 | 0.0 | 0.0 | 0.0 | 0.0 | 0.0 | 0.0 |
| 51a | 8.000 | 9.0 | | | 9.0 | 9.0 | | 9.0 | 9.0 | 6.0 | 0.0 | 0.0 | 5.0 |
| | 4.000 | 7.0 | | | 9.0 | 3.0 | | 9.0 | 8.0 | 8.0 | 0.0 | 0.0 | 0.0 |
| | 2.000 | 9.0 | 9.0 | 9.0 | 9.0 | 8.0 | 9.0 | 9.0 | 2.5 | 2.5 | 0.0 | 0.0 | 0.0 |
| | 1.000 | 6.0 | 9.0 | 9.0 | 3.0 | 2.5 | 9.0 | 8.0 | 0.0 | 0.0 | 0.0 | 0.0 | 0.0 |
| | .500 | 0.0 | 5.0 | 5.0 | 0.0 | 0.0 | 9.0 | 5.0 | 0.0 | 0.0 | 0.0 | 0.0 | 0.0 |
| | .250 | 0.0 | 0.0 | 0.0 | 0.0 | 0.0 | 9.0 | 0.0 | 0.0 | 0.0 | 0.0 | 0.0 | 0.0 |
| | .125 | 0.0 | 0.0 | 0.0 | 0.0 | 0.0 | 5.0 | 0.0 | 0.0 | 0.0 | 0.0 | 0.0 | 0.0 |
| 50b | 8.000 | 8.0 | 9.0 | 9.0 | 9.0 | 9.0 | | 9.0 | 9.0 | 9.0 | 3.0 | 0.0 | 5.0 |
| | 2.000 | 0.0 | 9.0 | 9.0 | 9.0 | 5.0 | | 9.0 | 9.0 | 9.0 | 0.0 | 0.0 | 0.0 |
| | 1.000 | 0.0 | 9.0 | 8.0 | 9.0 | 3.0 | | 9.0 | 9.0 | 7.0 | 0.0 | 0.0 | 5.0 |
| | .500 | 0.0 | 5.0 | 0.0 | 7.0 | 0.0 | | 9.0 | 9.0 | 0.0 | 0.0 | 0.0 | 0.0 |
| | .250 | 0.0 | 3.0 | 0.0 | 4.0 | 0.0 | | 7.0 | 3.0 | 0.0 | 0.0 | 0.0 | 0.0 |
| | .125 | 0.0 | 0.0 | 0.0 | 0.0 | 0.0 | | 0.0 | 0.0 | 0.0 | 0.0 | 0.0 | 0.0 |
| 29a | 8.000 | 9.0 | 9.0 | 8.0 | 9.0 | 8.0 | 9.0 | 9.0 | 9.0 | 9.0 | 0.0 | 0.0 | 5.0 |
| | 2.000 | 9.0 | 9.0 | 5.0 | 9.0 | 2.0 | 9.0 | 9.0 | 2.0 | 2.0 | 0.0 | 0.0 | 4.0 |
| | 1.000 | 5.0 | 5.0 | 0.0 | 7.0 | 0.0 | 9.0 | 9.0 | 0.0 | 0.0 | 0.0 | 0.0 | 0.0 |
| | .500 | 3.0 | 0.0 | 0.0 | 5.0 | 0.0 | 9.0 | 5.0 | 0.0 | 0.0 | 0.0 | 0.0 | 0.0 |
| | .250 | 0.0 | 0.0 | 0.0 | 0.0 | 0.0 | 9.0 | 0.0 | 0.0 | 0.0 | 0.0 | 0.0 | 0.0 |
| 60a | 8.000 | 9.0 | 9.0 | 9.0 | 9.0 | 9.0 | | 9.0 | 9.0 | 9.0 | 5.0 | 0.0 | 5.0 |
| | 2.000 | | 9.0 | 9.0 | 9.0 | 9.0 | | 9.0 | 9.0 | 9.0 | 4.0 | 0.0 | 4.0 |
| | 1.000 | | 9.0 | 9.0 | 9.0 | 5.0 | | 9.0 | 9.0 | 9.0 | 4.0 | 0.0 | 1.0 |
| | .500 | | 9.0 | 7.0 | 9.0 | 4.0 | | 9.0 | 9.0 | 9.0 | 2.0 | 0.0 | 0.0 |
| | .250 | | 7.0 | 0.0 | 5.0 | 0.0 | | 0.0 | 3.0 | 0.0 | 0.0 | 0.0 | 0.0 |
| 24j | 8.000 | 8.0 | | | 9.0 | 9.0 | | 9.0 | 9.0 | 9.0 | 7.0 | 0.0 | 6.0 |
| | 2.000 | | 9.0 | 9.0 | 9.0 | 9.0 | | 9.0 | 9.0 | 9.0 | 4.0 | 0.0 | 4.0 |
| | 1.000 | | 9.0 | 9.0 | 9.0 | 8.0 | | 9.0 | 1.0 | 0.0 | 0.0 | 0.0 | 0.0 |
| | .500 | | 8.0 | 7.0 | 9.0 | 7.0 | | 9.0 | 0.0 | 4.0 | 0.0 | 0.0 | 4.0 |
| | .250 | | 1.0 | 1.0 | 5.0 | 5.0 | | 0.0 | 0.0 | 0.0 | 0.0 | 0.0 | 2.0 |
| | .125 | | | | | 3.0 | | 9.0 | 0.0 | 0.0 | 0.0 | 0.0 | 1.0 |
| 50c | 8.000 | 9.0 | | | 9.0 | 9.0 | | 9.0 | 9.0 | 3.0 | 0.0 | 2.0 | 0.0 |
| | 2.000 | | 9.0 | 9.0 | 9.0 | 5.0 | | 9.0 | 6.0 | 2.0 | 0.0 | 0.0 | 0.0 |
| | 1.000 | | 9.0 | 9.0 | 9.0 | 3.0 | | 9.0 | 0.0 | 2.0 | 0.0 | 0.0 | 0.0 |
| | .500 | | | | | | | | | | | | |

TABLE VIII-continued

PRE-EMERGENCE TESTS - RATES IN KG/HA

| Compound of Example No. | RATE | BARNYARDGR | CANARYGRAS | CRABGRASS | GREEN FOX | WILD OATS | MATRI CARIA | WILD MUSTD | PRIKY SIDA | PENN SMART | CORN FIELD | COTTON | W WHEAT NU |
|---|---|---|---|---|---|---|---|---|---|---|---|---|---|
| | .250 | | 9.0 | 9.0 | 9.0 | 0.0 | | 9.0 | 0.0 | 3.0 | 0.0 | 0.0 | 0.0 |
| | .125 | | 8.0 | 6.0 | 3.0 | 0.0 | | 3.0 | 0.0 | 1.0 | 0.0 | 0.0 | 0.0 |
| 50d | 8.000 | 8.0 | | | | | | | | | | | |
| | 2.000 | | 9.0 | 9.0 | 9.0 | 9.0 | | 9.0 | 9.0 | 8.0 | 0.0 | 3.0 | 4.0 |
| | 1.000 | | 9.0 | 9.0 | 9.0 | 8.0 | | 9.0 | 9.0 | 4.0 | 0.0 | 3.0 | 3.0 |
| | .500 | | 9.0 | 7.0 | 9.0 | 8.0 | | 9.0 | 9.0 | 4.0 | 0.0 | 3.0 | 3.0 |
| | .250 | | 9.0 | 6.0 | 5.0 | 4.0 | | 9.0 | 1.0 | 4.0 | 0.0 | 3.0 | 3.0 |
| | .125 | | 9.0 | 5.0 | 0.0 | 2.0 | | 5.0 | 0.0 | 4.0 | 0.0 | 3.0 | 2.0 |
| 29b | 8.000 | 8.0 | | | | | | | | | | | |
| | 2.000 | | | 9.0 | 9.0 | 8.0 | | 9.0 | 9.0 | 9.0 | 7.0 | 9.0 | 8.0 |
| | 1.000 | | | 9.0 | 9.0 | 9.0 | | | 9.0 | 9.0 | 7.0 | 8.0 | 6.0 |
| | .500 | | | 9.0 | 9.0 | 7.0 | | | 9.0 | 9.0 | 4.0 | 5.0 | 3.0 |
| | .250 | | | 7.0 | 5.0 | 3.0 | | | 3.0 | 3.0 | 0.0 | 4.0 | 1.0 |
| | .125 | | | 6.0 | 3.0 | 0.0 | | | 3.0 | 3.0 | 0.0 | 5.0 | 1.0 |

What is claimed is:

1. A compound having the formula:

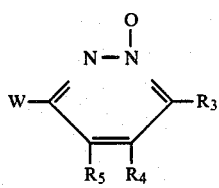

wherein R₃ is H or OCH₃; R₄ is CH₃, CH₂OCH₃ or C₂H₅; R₅ is H or CH₃; W is 2-thienyl, 3-thienyl, cyclohexyl, phenyl or phenyl substituted with one or two substituents selected from Cl, F, CH₃, OCH₃, CF₃, OCHF₂, OC₆H₅ or OCF₃.

2. A compound according to claim 1, 5-methyl-3(α,α,α-trifluoro-m-tolyl)pyridazine-1-oxide.

3. A compound according to claim 1, 5-methyl-3-[m-(trifluoromethoxy)phenyl]pyridazine-1-oxide.

4. A compound 6-cyclohexyl-3-(dimethylamino)-4-methylpyridazine.

5. A compound 3-cyclohexyl-6-methoxy-4,5-dimethylpyridazine.

6. A compound 3-dimethylamino-4-methyl-6-(2-thienyl)pyridazine.

7. A compound 3-[m-(di—fluoromethoxy)phenyl]-5-methylpyridazine.

8. A compound 6-(m-chlorophenyl)-3-methoxy-4-methylpyridazine.

9. A compound 3-methoxy-4-methyl-6-(m-phenoxyphenyl)-pyridazine.

10. A compound 3-methoxy-4-methyl-6-(3-pyridyl)-pyridazine.

11. A compound 3-methoxy-4-methyl-6-(4-pyridyl)-pyridazine.

12. A compound 3-methoxy-4-methyl-6-(3-thienyl)-pyridazine.

13. A compound Carbazic acid, 3-[4-methyl-6-(α,α,α-trifluoro-m-tolyl)-3-pyridazinyl-, ethyl ester.

14. A compound 3-dimethylamino-4-methyl-6-(α,α,α-trifluoro-m-tolyl)-pyridazine.

15. A compound 3-chloro-6-[m-(difluoromethoxy)phenyl]-4-methyl]-pyridazine.

16. A compound 5-methyl-3-(α,α,α-trifluoro-m-tolyl)pyridazine-1-oxide.

17. A herbicidal composition for the preemergence and postemergence control of undesirable plant species comprising an inert solid or liquid diluent, a surfactant, and a herbicidally-effective amount of a compound having the formula:

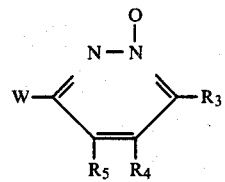

wherein R₃ is H or OCH₃; R₄ is H, CH₃, C₂H₅ or CH₂OCH₃; R₅ is H or CH₃; W is 2-thienyl, 3-thienyl, cyclohexyl, methylcyclohexyl, or

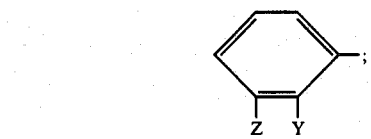

Y is H, Cl, F or CH₃; Z is H, Cl, F, CN, CH₃, OCH₃, CF₃, OCHF₂ or OCF₃.

18. A method for the control of undesirable plant species comprising applying to the foliage thereof or to soil containing seeds or other propagating organs of said undesirable plant species, a herbicidally-effective amount of a compound having the formula:

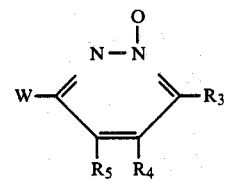

wherein R₃ is H or OCH₃; R₄ is H, CH₃, CH₂OCH₃ or C₂H₅; R₅ is H or CH₃; W is 2-thienyl, 3-thienyl, cyclohexyl, methylcyclohexyl; phenyl or phenyl substituted with one or two substituents selected from Cl, F, CH₃, CF₃ CN, OCHF₂, OC₆H₅, OCH₃, or OCF₃.

19. A method according to claim 15 for the preemergence control of undesirable plant species comprising; applying to soil containing seeds or other propagating organs of said undesirable plant species, about 0.25 kg/ha to about 10 kg/ha of a compound in said claim 18.

20. A method according to claim 18 for the control of undesirable plant species comprising; applying to the foliage of said undesirable plants about 0.25 kg/ha to about 10.0 kg/ha of a compound in said claim 18.

* * * * *